(12) United States Patent
Ozawa et al.

(10) Patent No.: US 8,408,788 B2
(45) Date of Patent: Apr. 2, 2013

(54) X-RAY IMAGE DIAGNOSTIC APPARATUS AND CONTROL METHOD OF X-RAY IMAGE DIAGNOSTIC APPARATUS

(75) Inventors: Masahiro Ozawa, Sakura (JP); Hajime Yoshida, Nasushiobara (JP); Nobuo Kobayashi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 301 days.

(21) Appl. No.: 12/980,989

(22) Filed: Dec. 29, 2010

(65) Prior Publication Data

US 2011/0170668 A1 Jul. 14, 2011

(30) Foreign Application Priority Data

Jan. 12, 2010 (JP) .................. 2010-004359

(51) Int. Cl.
*H05G 1/02* (2006.01)

(52) U.S. Cl. ...................................... 378/197

(58) Field of Classification Search ............... 378/62, 378/117, 193–197, 207
See application file for complete search history.

(56) References Cited

FOREIGN PATENT DOCUMENTS

JP 2004-160263 6/2004

*Primary Examiner* — Courtney Thomas
(74) *Attorney, Agent, or Firm* — Oblon, Spivak, McClelland, Maier & Neustadt, L.L.P.

(57) ABSTRACT

An X-ray image diagnostic apparatus has an X-ray irradiating unit, a receiving unit, a supporting unit, a registering unit, a calculating unit and a presenting unit. The X-ray irradiating unit irradiates an X-ray. The receiving unit receives the X-ray. The supporting unit supports the X-ray irradiating unit and the receiving unit to be opposed to each other, and the supporting unit is movable in a room. The registering unit registers in advance a target position after movement of the supporting unit. The calculating unit calculates a track of the supporting unit from a present position to the registered target position. The presenting unit presents the track until the supporting unit moves to reach the register target position. For example, the registering unit registers a target position coordinate and a target vertical axis rotation angle of the supporting unit as the target position.

18 Claims, 14 Drawing Sheets

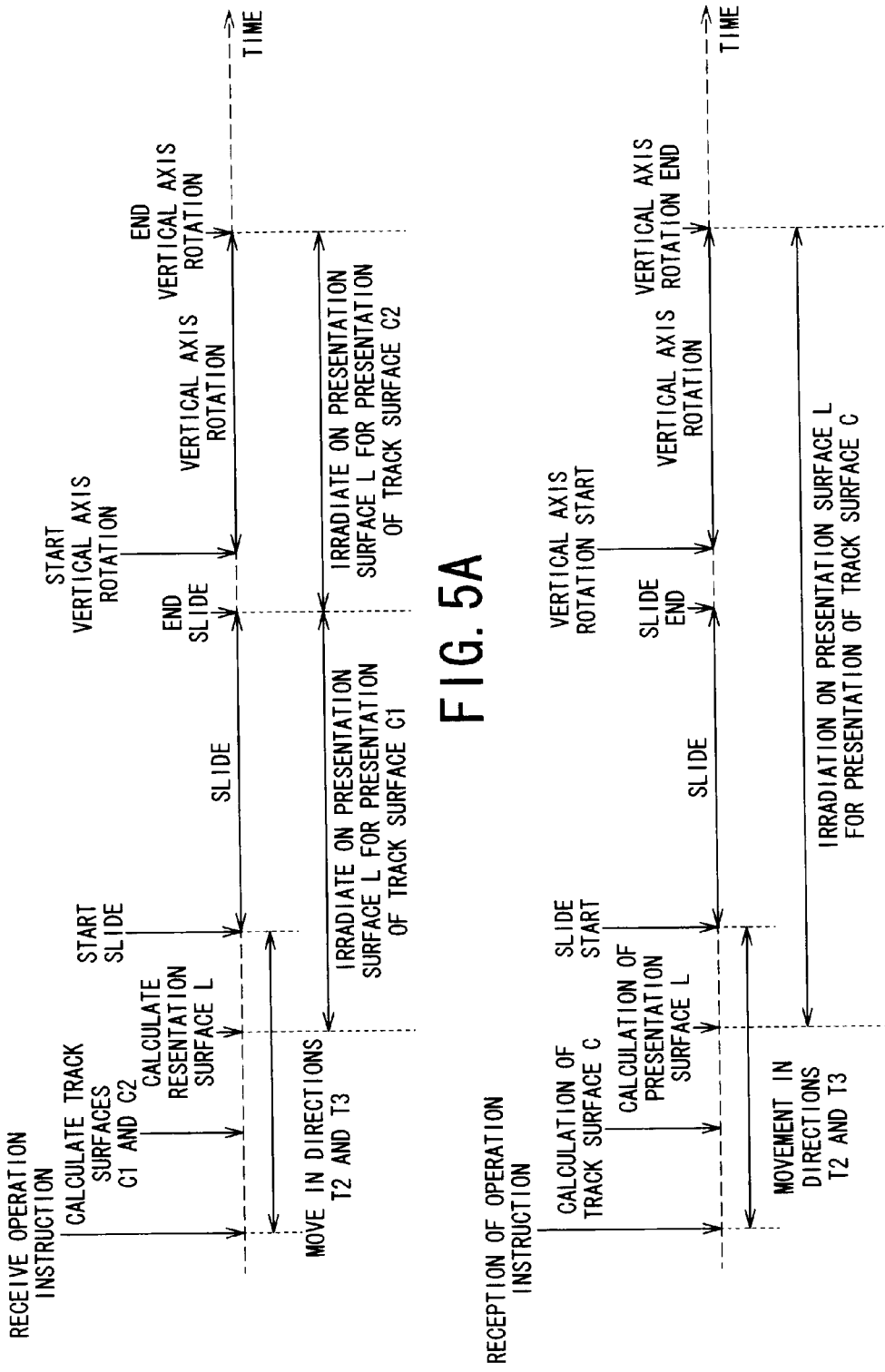

X-RAY IMAGE DIAGNOSTIC APPARATUS AND CONTROL METHOD OF X-RAY IMAGE DIAGNOSTIC APPARATUS

CROSS-REFERENCE TO RELATED APPLICATION

This application is based upon and claims the benefit of priority from Japanese Patent Application No. 2010-4359, filed on Jan. 12, 2010, the entire contents of which are incorporated herein by reference.

FIELD

An embodiment as a mode of the present invention relates to an X-ray image diagnostic apparatus and a control method of the X-ray image diagnostic apparatus including an overhead traveling C-arm or a floor traveling C-arm.

BACKGROUND

An X-ray image diagnostic apparatus as a cardiovascular X-ray diagnostic system is used as an apparatus that supports interventional radiology (IVR). In some case, in percutaneous coronary intervention (PCI) and an examination, contrast check for lower limb arteries is performed after a series of coronary artery contrast and treatment because there may be complication of a constrictive disease of lower limb arteries.

An X-ray image diagnostic apparatus including an overhead traveling C-arm is set in a surgical operating room to realize an environment in which a vascular surgeon and cardiovascular internist perform treatment of a cardiovascular disease in cooperation with each other. This makes it unnecessary to move a patient between the surgical operating room and a catheter examination room and makes it possible to perform quicker treatment. Such a system is called Hybrid OR system.

A technique that is suitable for a practitioner to perform X-ray photographing while performing treatment and allows the practitioner to arrange a patient at height for easy work according to treatment content is disclosed.

In the Hybrid OR system, during an operation by the vascular surgeon, the overhead traveling C-arm of the cardiovascular X-ray diagnostic system is set at a position coordinate and a vertical rotation angle not obstructing the operation. Next, in an operation by the cardiovascular internist, the overhead traveling C-arm needs to be moved from the position coordinate and the vertical rotation angle to a position coordinate and a vertical axis rotation angle for enabling the cardiovascular internist to immediately start photographing of an object P. When the overhead traveling C-arm is moved, since there are many axes of movement of a mechanism to be controlled, it is not easy to manually operate the overhead traveling C-arm. Therefore, an auto-positioning function is used. With the auto-positioning function, the cardiovascular internist performs simple operation such as number input to automatically move the overhead traveling C-arm to the position coordinate and the vertical rotation angle not obstructing the operation registered in advance and the position coordinate and the vertical axis rotation angle for enabling the cardiovascular internist to immediately start photographing of the object P.

However, with the auto-positioning function, in order to prevent collision with equipment and medical staff present in the surgical operating room, the cardiovascular internist performs moving operation for the overhead traveling C-arm little by little while checking surroundings of the overhead traveling C-arm. This takes labor and time. When a medical staff member unaccustomed to the system performs the moving operation, since the medical staff member cannot accurately grasp in which direction the overhead traveling C-arm moves next, the overhead traveling C-arm moves in a direction unintended by the operator. As a result, collision with equipment or the like in the room is likely to occur.

In order to prevent such risks, in some case, the operator performs manual operation to move the overhead traveling C-arm in a direction intended by the operator without using the auto-positioning function, although this takes time. In this case, work burden on the operator is large.

Not only in the hybrid OR system but also in the cardiovascular X-ray diagnostic system, the same problems could occur when the overhead traveling C-arm or the floor traveling C-arm needs to be moved according to a situation of an examination or treatment such as movement of a biplane system to a lateral side.

BRIEF DESCRIPTION OF THE DRAWINGS

In accompanying drawings,

FIGS. 5A and 5B are time charts showing a relation between a combined operation of a slide and a vertical axis rotation of the C-arm shown in FIGS. 4A to 4E and timing for calculation of the track surface and the presentation surface;

DETAILED DESCRIPTION

An X-ray image diagnostic apparatus and a control method of the X-ray image diagnostic apparatus according to an embodiment of the present invention is explained with reference to accompanying drawings.

To solve the above-described problems, the X-ray image diagnostic apparatus according to the present embodiment has: an X-ray irradiating unit configured to irradiate an X-ray; a receiving unit configured to receive the X-ray; a supporting unit configured to support the X-ray irradiating unit and the receiving unit to be opposed to each other, the supporting unit being movable in a room; a registering unit configured to register in advance a target position after movement of the supporting unit; a calculating unit configured to calculate a track of the supporting unit from a present position to the registered target position; and a presenting unit configured to present the track until the supporting unit moves to reach the register target position.

To solve the above-described problems, the control method of the X-ray image diagnostic apparatus having: an X-ray irradiating unit configured to irradiate an X-ray; a receiving unit configured to receive the X-ray; and a supporting unit configured to support the X-ray irradiating unit and the receiving unit to be opposed to each other, the supporting unit being movable in a room, has: a registering step for registering in advance a target position after movement of the supporting unit; a calculating step for calculating a track of the supporting unit from a present position to the registered target position; and a presenting step for presenting the track until the supporting unit moves to reach the register target position.

Figure 1:
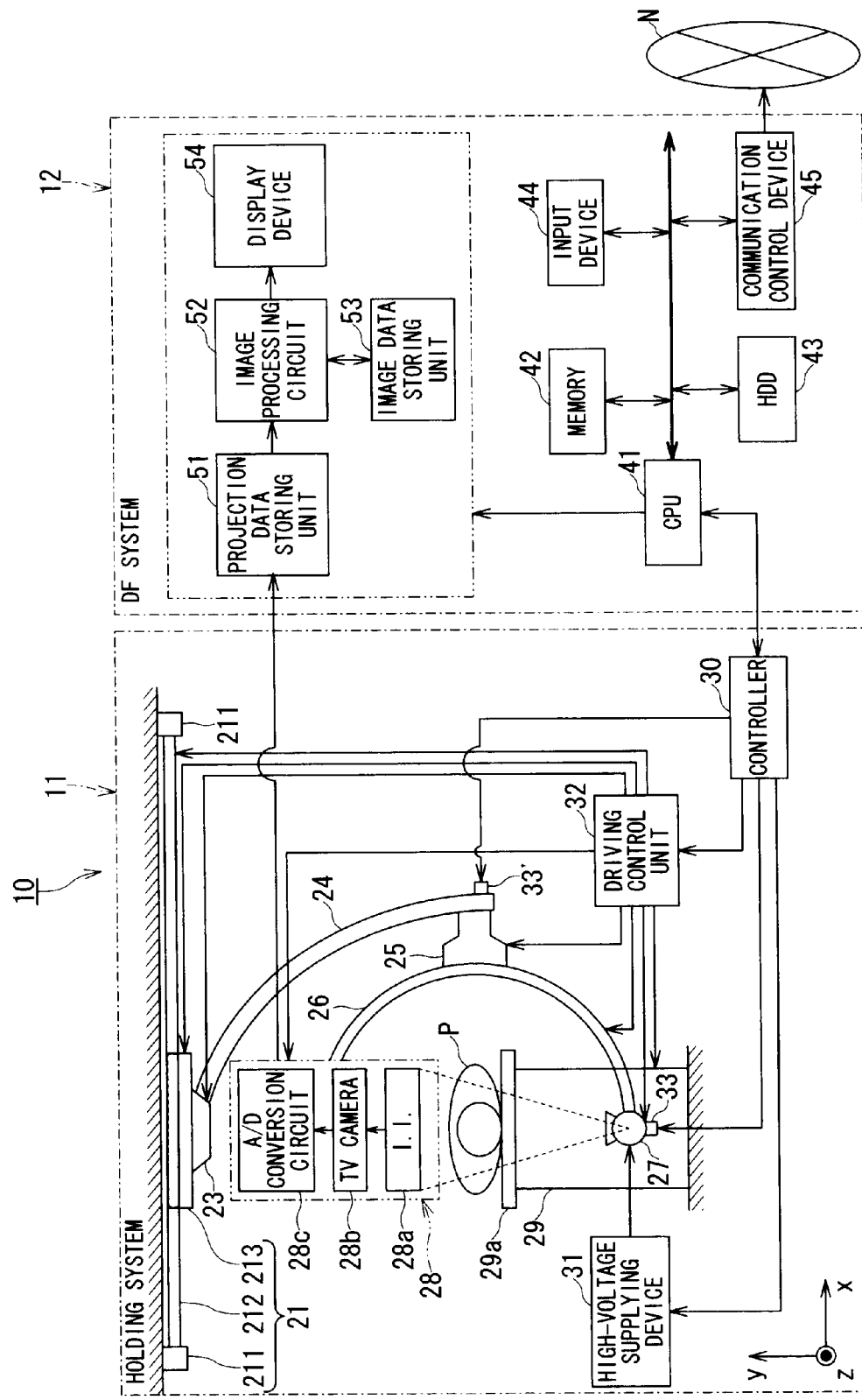
FIG. 1 is a schematic diagram showing a hardware configuration of an X-ray image diagnostic apparatus according to a present embodiment.
Figure 2:
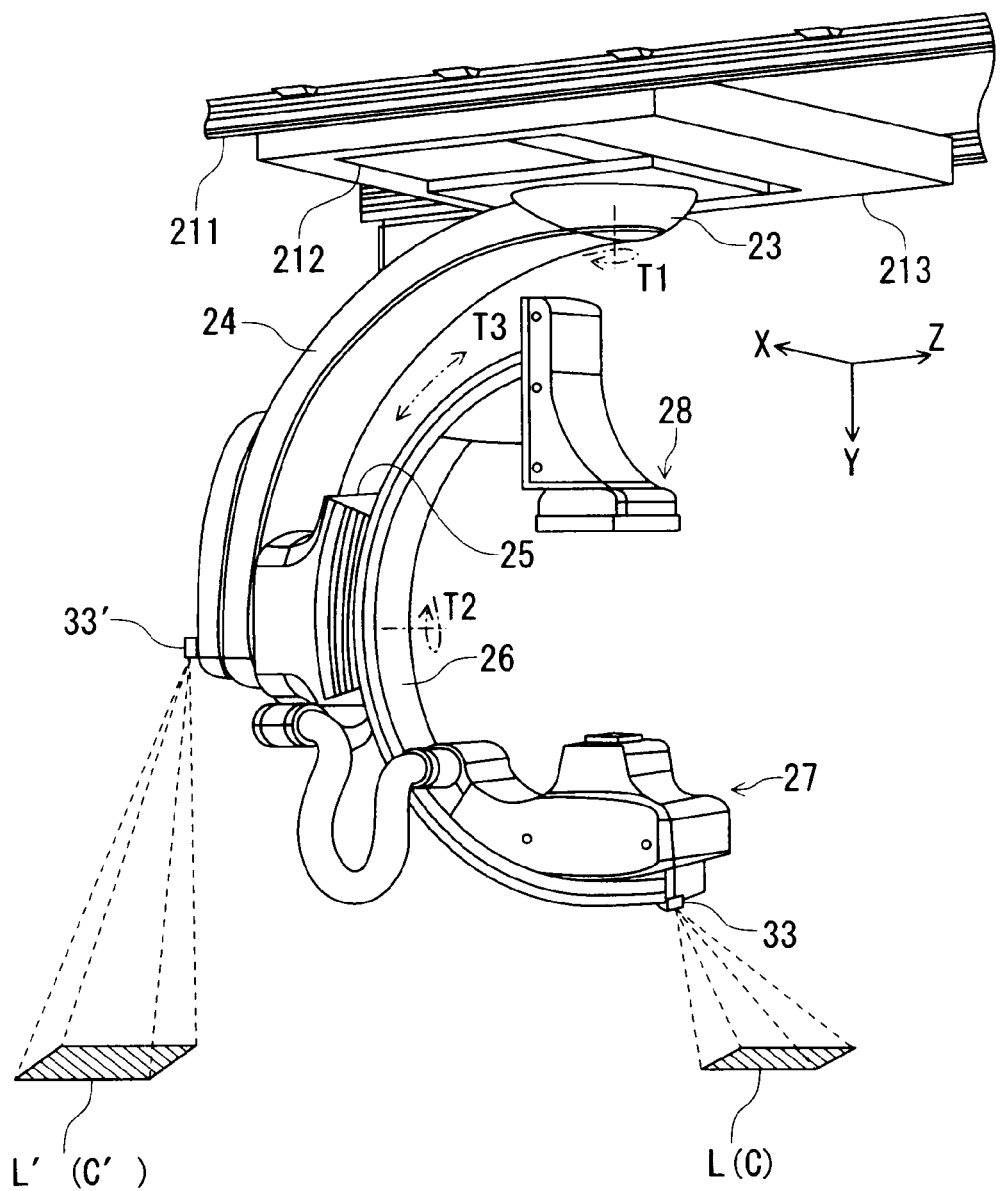
FIG. 2 is a perspective view showing an external configuration of a holding system in the X-ray image diagnostic apparatus according to the present embodiment.

FIG. 1 is a schematic diagram showing a hardware configuration of the X-ray image diagnostic apparatus according to the present embodiment. FIG. 2 is a perspective view showing an external configuration of a holding system in the X-ray image diagnostic apparatus according to the present embodiment.

FIGS. 1 and 2 show an X-ray image diagnostic apparatus 10 including an overhead traveling C-arm according to the present embodiment. The X-ray image diagnostic apparatus 10 roughly includes a holding system 11 and a DF (digital fluorography) system 12. In general, the holding system 11 and the DF system 12 are set in a surgical operating room (an examination and treatment room). An X-ray image diagnostic apparatus according to the present invention is not limited to the X-ray image diagnostic apparatus 10 including the overhead traveling C-arm and may be an X-ray image diagnostic apparatus including a floor traveling C-arm.

The holding system 11 includes a slide mechanism 21, a vertical axis rotating mechanism 23, a suspended arm 24, a C-arm rotating mechanism 25, a C-arm 26, an X-ray irradiating device 27, a receiving device 28, a bed 29, a controller 30, a high-voltage supplying device 31, a driving control unit 32, and a laser beam source 33.

The slide mechanism 21 includes a Z-axis direction rail 211, an X-axis direction rail 212, and a carriage 213. The slide mechanism 21 slides, according to the control by the controller 30 via the driving control unit 32, the vertical axis rotating mechanism 23, the suspended arm 24, the C-arm rotating mechanism 25, the C-arm 26, the X-ray irradiating device 27, and the receiving device 28 integrally in a horizontal direction.

The Z-axis direction rail 211 is extended in a Z-axis direction (a major axis direction of a table-top 29a) and supported by a ceiling.

The X-axis direction rail 212 is extended in an X-axis direction (a minor axis direction of the table-top 29a) and supported by the Z-axis direction rail 211 via rollers (not shown) at both ends of the X-axis direction rail 212. The X-axis direction rail 212 is moved in the Z-axis direction on the Z-axis direction rail 211 according to the control by the controller 30 via the driving control unit 32.

The carriage 213 is supported by the X-axis direction rail 212 via a roller (no shown). The carriage 213 is moved in the X-axis direction on the X-axis direction rail 212 according to the control by the controller 30 via the driving control unit 32.

The X-axis direction rail 212 that supports the carriage 213 is movable in the Z-axis direction on the Z-axis direction rail 211. The carriage 213 is movable in the X-axis direction on the X-axis direction rail 212. Therefore, the carriage 213 is movable in the horizontal direction (the X-axis direction and the Z-axis direction).

The vertical axis rotating mechanism 23 is rotatably supported by the carriage 213. The vertical axis rotating mechanism 23 rotates, according to the control by the controller 30 via the driving control unit 32, the suspended arm 24, the C-arm rotating mechanism 25, the C-arm 26, the X-ray irradiating device 27, and the receiving device 28 integrally in a vertical axis rotating direction T1 (shown in FIG. 2).

The suspended arm 24 is supported by the vertical axis rotating mechanism 23.

The C-arm rotating mechanism 25 is rotatably supported by the suspended arm 24. The C-arm rotating mechanism 25 rotates, according to the control by the controller 30 via the driving control unit 32, the C-arm 26, the X-ray irradiating device 27, and the receiving device 28 integrally in a rotating direction T2 (shown in FIG. 2) with respect to the suspended arm 24.

The C-arm 26 is supported by the C-arm rotating mechanism 25. The X-ray irradiating device 27 and the receiving device 28 are arranged to be opposed to each other across the object P. A rail (not shown) is provided on a back or a side of the C-arm 26. The rail is held between the C-arm rotating mechanism 25 and the C-arm 26. The C-arm 26 causes, according to the control by the controller 30 via the driving control unit 32, the X-ray irradiating device 27 and the receiving device 28 to perform arcuate motion integrally in an arc direction T3 (shown in FIG. 2) of the C-arm 26.

The X-ray irradiating device 27 is provided at one end of the C-arm 26. The X-ray irradiating device 27 is provided to be movable back and forth according to the control by the controller 30 via the driving control unit 32. The X-ray irradiating device 27 receives supply of high-voltage power from the high-voltage supplying device 31 and irradiates an X-ray toward a predetermined region of the object P according to a condition of the high-voltage power. The X-ray irradiating device 27 includes, on an emission side of the X-ray, an X-ray irradiation stop including plural lead vanes and a compensation filter that is formed of silicon rubber or the like and attenuates a predetermined amount of irradiated X-ray in order to prevent halation.

The receiving device 28 is provided at the other end of the C-arm 26 and on an emission side of the X-ray irradiating device 27. The receiving device 28 is provided to be movable back and forth according to the control by the controller 30 via the driving control unit 32. The receiving device 28 is an I. I. (image intensifier)—TV system and roughly includes an I. I. 28a, a TV camera 28b, and an A/D (analog to digital) conversion circuit 28c. The I. I. 28a converts an X-ray transmitted through the object P and an X-ray directly made incident on the I. I. 28a and performs multiplication of luminance in a process of conversion from light to electrons and the electrons to light to form highly sensitive projection data. The TV camera 28b converts optical projection data into an electric signal using a CCD (charge coupled device) imaging element. The A/D conversion circuit 28c converts a time-series analog signal (video signal) output from the TV camera 28b into a digital signal.

Note that the receiving device 28 may include a flat panel detector (FPD). When the receiving device 28 includes the flat panel detector, the receiving device 28 detects an X-ray using two-dimensionally-arrayed detection elements and converts the X-ray into an electric signal.

The bed 29 is supported on a floor surface and supports a table-top (a catheter table) 29a. The bed 29 moves the table-top 29a horizontally (in the X and Z-axis directions) and vertically (in a Y-axis direction) and rolls the table-top 29a according to the control by the controller 30 via the driving control unit 32. The object P is placed on the table-top 29a. In the following explanation, the holding system 11 is a holding system of an under-tube type in which the X-ray irradiating device 27 is located below the table-top 29a. However, the holding system 11 may be a holding system of an over-tube type in which the X-ray irradiating device 27 is located above the table-top 29a.

The controller 30 includes a CPU (central processing unit) and a memory not shown in the figure. The controller 30 controls operations of the high-voltage supplying device 31, the driving control unit 32, the laser beam source 33, a laser beam source 33', and the like.

The high-voltage supplying device 31 supplies high-voltage power to the X-ray irradiating device 27 according to the control by the controller 30.

The deriving control unit 32 drives the slide mechanism 21, the vertical axis rotating mechanism 23, the C-arm rotating mechanism 25, the C-arm 26, the X-ray irradiating device 27, the receiving device 28, and the table-top 29a of the bed 29 according to the control by the controller 30.

The laser beam source 33 presents a slide track of the C-arm 26 following a slide of the carriage 213 by the slide mechanism 21 and a vertical axis slide track of the C-arm 26 following vertical axis rotation of the vertical axis rotating mechanism 23. For example, the laser beam source 33 is provided at a lower end of the C-arm 26 (in the case of the under tube type, at a lower end on the X-ray irradiating device 27 side) and on a major axis A (shown in FIG. 6A) of the C-arm 26 viewed from above. The laser beam source 33 spatially irradiates a laser beam toward a presentation surface L for presenting a C-arm track to an operator on a track surface C obtained by projecting the slide track of the C-arm 26 and the vertical axis rotation track of the C-arm 26 on a floor surface (the presentation surface L is the same as the track surface C or included in the track surface C). The laser beam source 33 is provided at an upper end of the C-arm 26 (in the case of the under-tube type, at a side end of the receiving device 28). In that case, the laser beam source 33 spatially irradiates the laser beam toward a presentation surface L for presenting a C-arm track to the operator on a track surface C obtained by projecting the slide track of the C-arm 26 and the vertical axis rotation track of the C-arm 26 on a ceiling surface.

Therefore, when an obstacle is present in an irradiation space of the laser beam irradiated from the laser beam source 33, the laser beam is directly irradiated on the obstacle.

In the X-ray image diagnostic apparatus 10, the laser beam source 33' is provided in the suspended arm 24 together with the laser beam source 33 or instead of the laser beam source 33. In that case, the laser beam source 33' irradiates a laser beam toward a presentation surface L' for presenting a C-arm track to the operator on a track surface C' obtained by projecting the slide track of the C-arm 26 and the vertical axis rotation track of the C-arm 26 on the floor surface (the presentation surface L' is the same as the track surface C' or included in the track surface C'). A specific calculation method for the track surface C and calculation method for the presentation surface L on the track surface C are explained later. In the following explanation, it is assumed that the X-ray image diagnostic apparatus 10 includes only the laser beam source 33.

The DF system 12 is configured on the basis of a computer. The DF system 12 mutually communicates with a network N such as a LAN (local area network) of a hospital main network. The DF system 12 roughly includes hardware components such as a CPU 41 as a processor, a memory 42, a HDD (hard disk drive) 43, an input device 44, a communication control device 45, a projection data storing unit 51, an image processing circuit 52, an image data storing unit 53, and a display device 54. The CPU 41 is mutually connected to the hardware components of the DF system 12 via a bus as a common signal transmission line. In some case, the DF system 12 includes a drive for recording media (not shown).

When an operator such as a physician or a technical expert operates the input device 44 to input a command, the CPU 41 executes a computer program stored in the memory 42. Alternatively, the CPU 41 loads, to the memory 42, a computer program stored in the HDD 43, a computer program transferred from the network N, received by the communication control device 45, and installed in the HDD 43, or a computer program read out from a storage medium, which is inserted in the drive for storage media (not shown), and installed in the HDD 43 and executes the computer program.

The memory 42 is a storage device having a configuration also including components such as a ROM (read only memory) and a RAM (random access memory). The memory 42 stores data of IPL (initial program loading) and BIOS (basic input/output system) and is used for a work memory of the CPU 41 and temporary storage of data.

The HDD 43 is a storage device having a configuration in which a metal HD (hard disk) applied or deposited with a magnetic substance is un-detachably incorporated. The HDD 43 stores computer programs (including an OS (operating system) besides application programs) installed in the DF system 12 and data. It is also possible to cause the OS to provide a GUI (graphical user interface) use many graphics for display of information to the operator and perform basic operation using the input device 44.

Examples of the input device 44 include a keyboard and a mouse operable by the operator. An input signal conforming to the operation is sent to the CPU 41. The input device 44 roughly includes a main console and a system console.

The communication control device 45 performs communication control corresponding to standards. The communication control device 45 has a function for connection to the network N through a telephone line. The DF system 12 is connectable to the network N via the communication control device 45.

The projection data storing unit 51 stores, according to the control by the CPU 41, projection data output from the A/D conversion circuit 28c of the holding system 11.

The image processing circuit 52 applies, according to the control by the CPU 41, logarithmic transformation processing (LOG processing) to the projection data stored in the projection data storing unit 51 and, if necessary, applies addition processing to the projection data. The image processing circuit 52 generates data of a fluoroscopic image and a photographing image (a DA image). The image processing circuit 52 applies image processing to the fluoroscopic image and the photographing image stored in the image data storing unit 53. Examples of the image processing include expansion/gradation/spatial filter processing for data, minimum/maximum trace processing for data accumulated in time series, and addition processing for removing noise. Data after the image processing by the image processing circuit 52 is output to the display device 54 and stored in a storage device such as the image data storing unit 53.

The image data storing unit 53 stores, according to the control by the CPU 41, the fluoroscopic image and the photographing image output from the image processing circuit 52 as data.

The display device 54 combines, according to the control by the CPU 41, examination information such as a patient name (character information of parameters, a scale, etc.) with the data of the fluoroscopic image and the photographing image generated by the image processing circuit 52 and, after D/A (digital to analog)—converting a combined signal, displays the combined signal as a video signal. The display device 54 includes a live monitor that displays live the fluoroscopic image and the photographing image output from the image processing circuit, a reference monitor that displays, as a still image, or reproduces and displays, as a moving image, the photographing image output from the image processing circuit 52, and a system monitor that displays mainly data for performing control of the holding system 11 such as data for FOV (field of view) switching.

Figure 3:
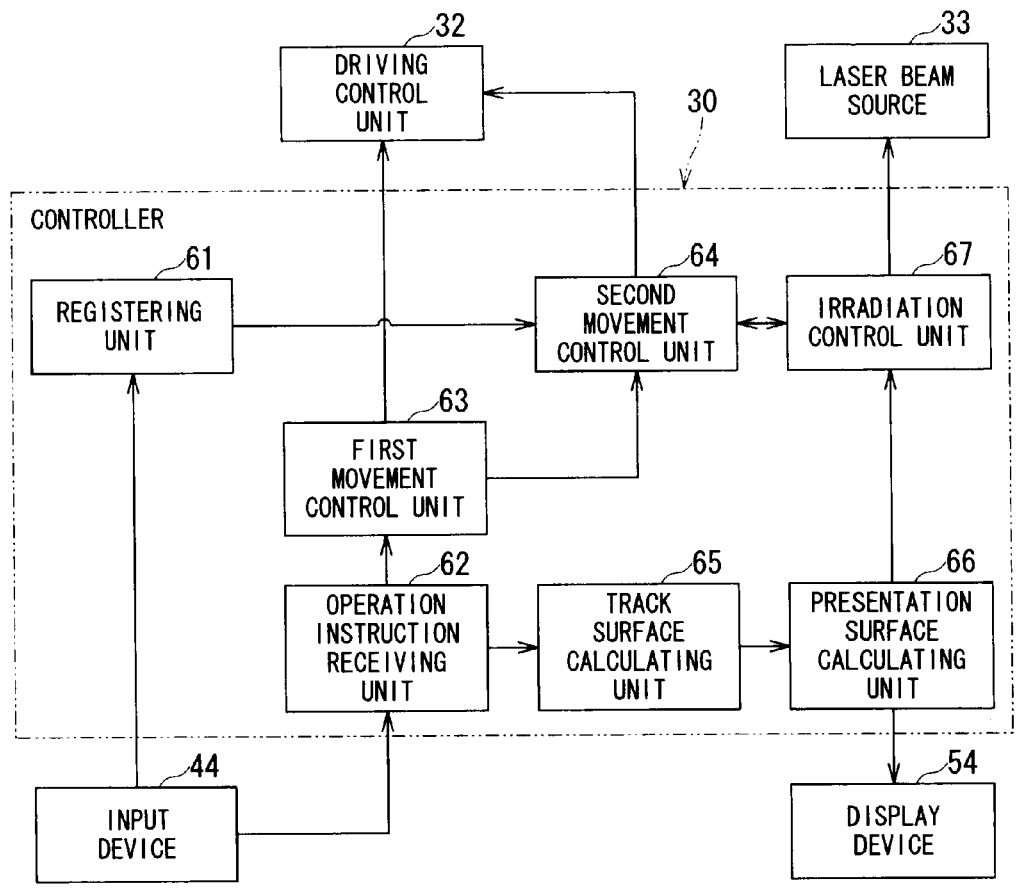
FIG. 3 is a block diagram showing functions of the X-ray image diagnostic apparatus according to the present embodiment.

FIG. 3 is a block diagram showing functions of the X-ray image diagnostic apparatus according to the present embodiment.

The controller 30 (or the CPU 41) shown in FIG. 1 executes computer programs, whereby, as shown in FIG. 3, the X-ray image diagnostic apparatus 10 functions as a registering unit 61, an operation instruction receiving unit 62, a first movement control unit 63, a second movement control unit 64, a track surface calculating unit 65, a presentation surface calculating unit 66, and an irradiation control unit 67. In the following explanation, it is assumed that the units 61 to 67 are included as the functions of the X-ray image diagnostic apparatus 10. However, all or a part of the units 61 to 67 may be included in the X-ray image diagnostic apparatus 10 as hardware.

The registering unit 61 has a function of registering in advance a target position (or target positions) after movement of the C-arm 26 (the carriage 213). The registering unit 61 registers a target position coordinate (X and Z-axis coordinate) of the C-arm 26 and a target vertical axis rotation angle of the C-arm 26. For example, the registering unit 61 registers the position coordinate and the vertical axis rotation angle in a surgical operating room away from the table-top 29a that do not obstruct an operation when a surgeon performs the operation on the object P on the table-top 29a. For example, when a cardiovascular internist performs an operation on the object P on the table-top 29a, the registering unit 61 registers the position coordinate and the vertical axis rotation angle for enabling the cardiovascular internist to immediately start photographing of the object P on the table-top 29a.

The registration by the registering unit 61 is performed by the operator performing a registration instruction using the input device 44 while actually performing the slide of the C-arm 26 and the vertical axis rotation of the C-arm 26. The registering unit 61 registers a required position coordinate and a required vertical axis rotation angle of the C-arm 26 in a storage device such as the memory of the controller 30.

The operation instruction receiving unit 62 has a function of receiving, from the input device 44, an operation instruction for movement of the C-arm 26 to the position coordinate and the vertical axis rotation angle registered by the registering unit 61.

The first movement control unit 63 has a function of controlling the driving control unit 32 and moving the C-arm 26 in the rotating direction T2 and the arc direction T3 to align the carriage 213, the X-ray irradiating device 27, and the receiving device 28 on a straight line when an operation instruction is received by the operation instruction receiving unit 62.

The second movement control unit 64 has a function of controlling the driving control unit 32 and driving the slide mechanism 21 to slide the C-arm 26 to the position coordinate registered by the registering unit 61 and controlling the driving control unit 32 and driving the vertical axis rotating mechanism 23 to rotate the C-arm 26 to the vertical axis rotation angle registered in the registering unit 61. The second movement control unit 64 only has to execute, according to a simple input (e.g., a number input) from the operator via the input device 44, the slide and the vertical axis rotation of the C-arm 26 for a period in which a movement instruction from the operator is valid (e.g., in a period in which a trigger switch is pressed). The order of operation of the slide and the vertical axis rotation of the C-arm 26 by the second movement control unit 64 may be any order. The slide and the vertical axis rotation of the C-arm 26 by the second movement control unit 64 do not simultaneously operate.

FIGS. 4A to 4E are top views schematically showing a process in which, when the operation instruction is received, the C-arm 26 is slid to the registered position coordinate and rotated around the vertical axis to the registered vertical axis rotation angle. When a registered position of the C-arm 26 is a position for enabling the operator to immediately start photographing of the object P on the table-top 29a, a positioning of the C-arm 26 is executed from a position shown in FIG. 4A to a position shown in FIG. 4E.

Figure 4A:
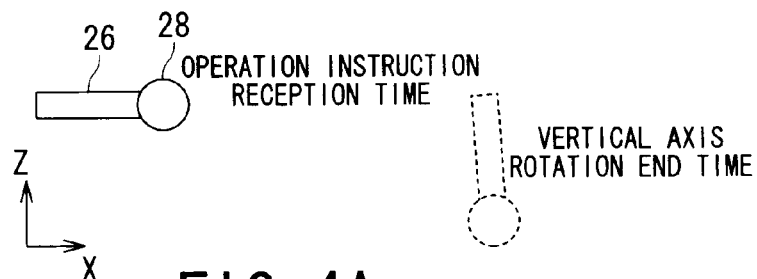
FIGS. 4A to 4E are top views schematically showing a process in which, when an operation instruction is received, a C-arm slid to a registered position coordinate and rotated around the vertical axis to the registered vertical axis rotation angle.

FIG. 4A shows the C-arm 26 at a position coordinate and a vertical axis rotation angle at the time of the reception of the operation instruction (a solid line) and the C-arm 26 at the registered position coordinate and the registered vertical axis rotation angle (at the time of the end of the vertical axis rotation) (a broken line). As shown in FIG. 4A, the position coordinate and the vertical axis rotation angle of the C-arm 26 in a state at the time of the reception of the operation instruction are different from the registered position coordinate and the registered vertical axis rotation angle.

Figure 4B:
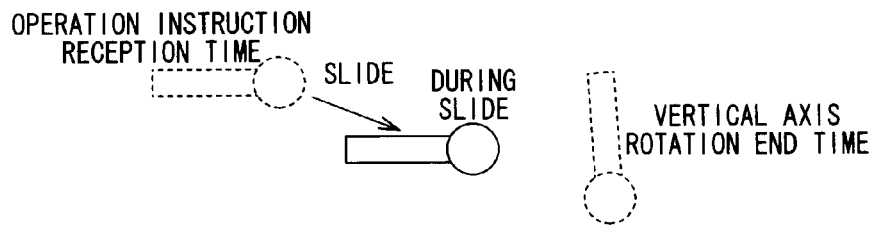

FIG. 4B shows the C-arm 26 at a position coordinate and a vertical axis rotation angle during a slide after FIG. 4A (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 4B, the position coordinate of the C-arm 26 during the slide are present between the position coordinate of the C-arm 26 at the time of the reception of the operation instruction shown in FIG. 4A and the registered position coordinate.

Figure 4C:

FIG. 4C shows the C-arm at a position coordinate and a vertical axis rotation angle at the time of end of the slide after FIG. 4B (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 4C, the position coordinate of the C-arm 26 at the time of the end of the slide coincides with the registered position coordinate.

Figure 4D:
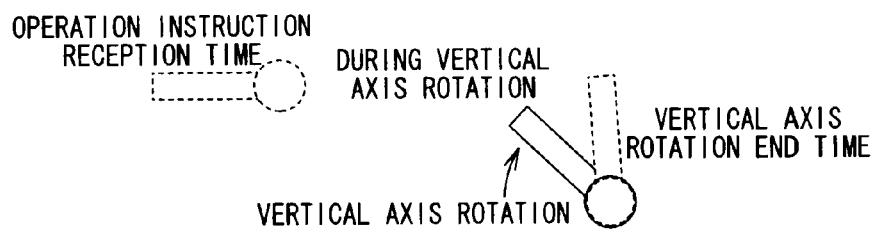

FIG. 4D shows the C-arm at a position coordinate and a vertical axis rotation angle during vertical axis rotation after FIG. 4C (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 4D, the vertical axis rotation angle of the C-arm 26 during the vertical axis rotation is present between the vertical axis rotation angle of the C-arm 26 at the time of the end of the slide shown in FIG. 4C and the registered vertical axis rotation angle.

Figure 4E:

FIG. 4E shows the C-arm 26 at a position coordinate and a vertical axis rotation angle at the time of end of the vertical axis rotation after FIG. 4D (a solid line) and the C-arm 26 at the position coordinate and the vertical axis rotation angle at the time of the reception of the operation instruction (a broken line). As shown in FIG. 4E, the vertical axis rotation angle of the C-arm 26 at the time of the end of the vertical axis rotation coincides with the registered vertical axis rotation angle. Therefore, according to FIGS. 4A to 4E, when the C-arm 26 is slid from the position coordinate of the C-arm 26 at the time of the reception of the operation instruction and the C-arm 26 is rotated around the vertical axis from the vertical axis rotation angle of the C-arm 26 at the time of the reception of the operation instruction, whereby the C-arm 26 coincides with the registered position coordinate and the registered vertical axis rotation angle.

The track surface calculating unit 65 shown in FIG. 3 has a function of, when an operation instruction is received by the operation instruction receiving unit 62, calculating a track of the C-arm 26 moving to the registered position coordinate and the vertical axis rotation angle from the time of the reception of the operation instruction (a major axis of the C-arm 26 viewed from above) and calculating the track surface C obtained by projecting the track of the C-arm 26 on the floor surface (a track surface C1 based on a slide and a track surface C2 based on vertical axis rotation). The track surface calculating unit 65 calculates the track surface C based on the track of the C-arm 26. However, the track surface calculating unit 65 is not limited to this. For example, the track surface calculating unit 65 may calculates a track surface based on tracks of the suspended arm 24 and the C-arm 26.

The presentation surface calculating unit 66 has a function of presenting a moving track of the C-arm 26 on the track surface C calculated by the track surface calculating unit 65 to the operator. For example, the presentation surface calculating unit 66 calculates the presentation surface L as an irradiation surface on which a laser beam is irradiated from the laser beam source 33.

The irradiation control unit 67 has a function of causing the laser beam source 33 to spatially irradiate a laser beam toward the presentation surface L calculated by the presentation surface calculating unit 66. The irradiation control unit 67 switches irradiation and non-irradiation of the laser beam according to an input signal input by the operator via the input device 44. The irradiation control unit 67 switches irradiation or non-irradiation of the laser beam according to whether the track of the C-arm 26 calculated by the track surface calculating unit 65 is equal to or longer than a predetermined distance (the presentation surface L is long).

FIGS. 5A and 5B are time charts showing a relation between a combined operation of the slide and the vertical axis rotation of the C-arm 26 shown in FIGS. 4A to 4E and timing for calculation of the track surface C and the presentation surface L.

FIG. 5A shows a first time chart in calculating the presentation surface L for presentation on the track surface C1 and the presentation surface L for presentation on the track surface C2. As shown in FIG. 5A, in the first time chart, when the operation instruction receiving unit 62 receives an operation instruction, the track surface calculating unit 65 calculates, while the C-arm 26 is moved in the rotating direction T2 and the arc direction T3 by the first movement control unit 63, the rectangular track surface C1 from the time of the reception of the operation instruction until the time of the end of the slide shown in FIGS. 4A to 4C. On the other hand, the track surface calculating unit 65 calculates the fan-shaped track surface C2 around the X-axis irradiation device 27 as a center of vertical axis rotation until the time of the end of the vertical axis rotation from the time of the end of the slide shown in FIGS. 4C to 4E. When the track surfaces C1 and C2 are calculated by the track surface calculating unit 65, the irradiation control unit 67 causes, in a period after the calculation of the track surface C1 until the time of the end of the slide, the laser beam source 33 to irradiate a laser beam toward the presentation surface L calculated for presentation on the track surface C1. On the other hand, the irradiation control unit 67 causes, in a period from the time of the end of the slide until the time of the end of the vertical axis rotation end, the laser beam source 33 to irradiate a laser beam toward the presentation surface L calculated for presentation on the track surface C2.

FIG. 5B shows a second time chart in calculating the presentation surface L for presentation on the track surfaces C1 and C2. As shown in FIG. 5B, when the operation instruction receiving unit 62 receives an operation instruction, the track surface calculating unit 65 calculates, while the C-arm 26 is moved in the rotating direction T2 and the arc direction T3 by the first movement control unit 63, the rectangular track surface C (the track surfaces C1 and C2) from the time of the reception of the operation instruction until the time of the end of the slide shown in FIGS. 4A to 4C. When the track surface C is calculated by the track surface calculating unit 65, the irradiation control unit 67 causes, in a period from the calculation of the track surface C until the time of the end of the vertical axis rotation end, the laser beam source 33 to irradiate a laser beam toward the presentation surface L calculated for presentation on the track surface C.

FIGS. 6A to 6E are top views schematically showing the transition of a presentation surface that occurs when the first time chart shown in FIG. 5A is used.

Figure 6A:
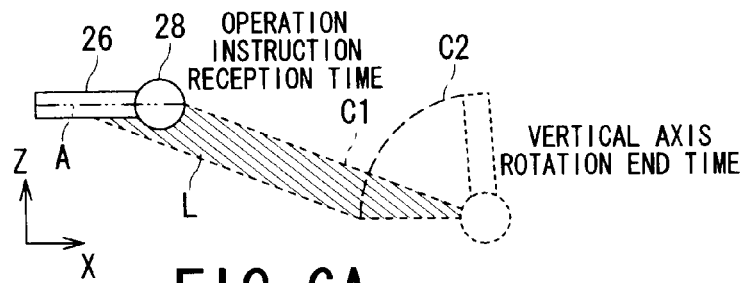
FIGS. 6A to 6E are top views schematically showing a transition of a presentation surface that occurs when the first time chart shown in FIG. 5A is used.

FIG. 6A shows, like FIG. 4A, the C-arm 26 at a position coordinate and a vertical axis rotation angle at the time of the reception of the operation instruction (a solid line) and the C-arm 26 at the registered position coordinate and the registered vertical axis rotation angle (at the time of end of the vertical axis rotation) (a broken line). As shown in FIG. 6A, the presentation surface calculating unit 66 at the time of the reception of the operation instruction (after the calculation of the track surface C1) calculates the presentation surface L that coincides with the track surface C1 calculated by the track surface calculating unit 65. The irradiation control unit 67 at the time of the reception of the operation instruction controls the laser beam source 33 to continuously or intermittently irradiate a laser beam toward the presentation surface L that coincides with the track surface C1.

Figure 6B:
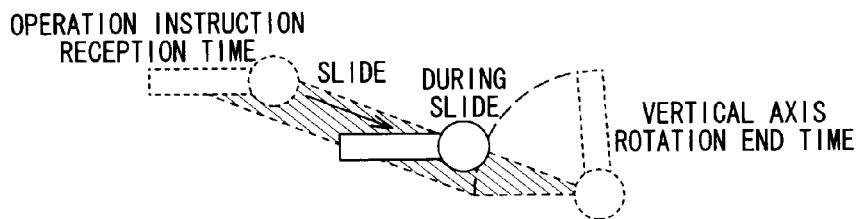

FIG. 6B shows, like FIG. 4B, the C-arm 26 at a position coordinate and a vertical axis rotation angle during a slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 6B, the irradiation control unit 67 during the slide controls the laser beam source 33 to continuously or intermittently irradiate a laser beam toward the presentation surface L that coincides with the track surface C1 calculated by the track surface calculating unit 65.

Figure 6C:
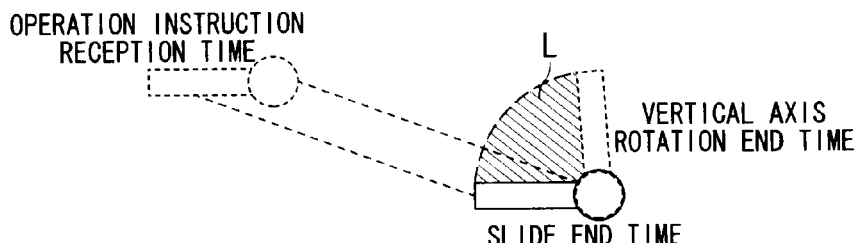

FIG. 6C shows, like FIG. 4C, the C-arm 26 at a position coordinate and a vertical axis rotation angle at the time of end of the slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 6C, the presentation surface calculating unit 66 at the time of the end of the slide calculates the presentation surface L that coincides with the track surface C2 calculated by the track surface calculating unit 65. The irradiation control unit 67 at the time of the end of the slide controls the laser beam source 33 to switch irradiation on the track surface C1 to irradiation on the track surface C2 and continuously or intermittently irradiate a laser beam toward the presentation surface L that coincides with the track surface C2.

Figure 6D:
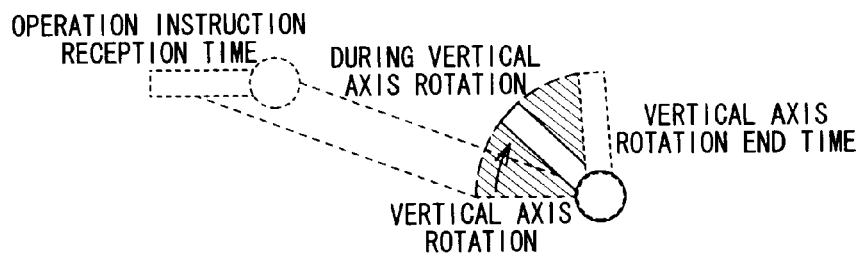

FIG. 6D shows, like FIG. 4D, the C-arm 26 at a position coordinate and a vertical axis rotation angle during vertical axis rotation (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 6D, the irradiation control unit 67 during the vertical axis rotation controls the laser beam source 33 to continuously or intermittently irradiate a laser beam toward the presentation surface L that coincides with the track surface C2 calculated by the track surface calculating unit 65.

Figure 6E:
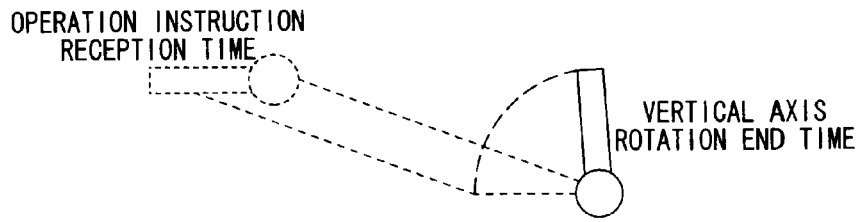

FIG. 6E shows, like FIG. 4E, the C-arm 26 at a position coordinate and a vertical axis rotation angle at the time of end of the vertical axis rotation (a solid line) and the C-arm 26 at the position coordinate and the vertical axis rotation angle at the time of the reception of the operation instruction (a broken line). As shown in FIG. 6E, the C-arm 26 at the time of the end of the vertical axis rotation is at the registered position coordinate and the registered vertical axis rotation angle and ends the movement. Therefore, the irradiation control unit 67 at the time of the end of the vertical axis rotation controls the laser beam source 33 to stop the irradiation of the laser beam.

In the explanation with reference to FIGS. 6A to 6E, the track surfaces C1 and C2 and the presentation surface L are always set to coincide with each other. However, the present invention is not limited to this. Modifications are explained with reference to FIGS. 7A to 7E, FIGS. 8A to 8E, and FIG. 9.

FIGS. 7A to 7E are top views schematically showing a sample of a modification of the transition of the presentation surface shown in FIGS. 6A to 6E.

Figure 7A:
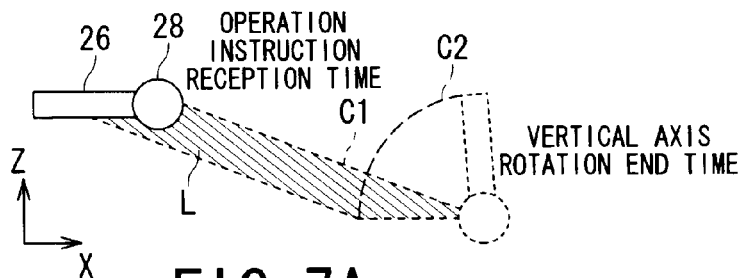
FIGS. 7A to 7E are top views schematically showing a sample of a modification of the transition of the presentation surface shown in FIGS. 6A to 6E.

FIG. 7A shows, like FIG. 4A, the C-arm 26 at a position coordinate and a vertical axis rotation angle at the time of the reception of the operation instruction (a solid line) and the C-arm 26 at the registered position coordinate and the registered vertical axis rotation angle (at the time of end of the vertical axis rotation) (a broken line). As shown in FIG. 7A, the presentation surface calculating unit 66 at the time of the reception of the operation instruction (after the calculation of the track surface C1) calculates the presentation surface L that coincides with the track surface C1 calculated by the track surface calculating unit 65. The irradiation control unit 67 at the time of the reception of the operation instruction controls the laser beam source 33 to continuously or intermittently irradiate a laser beam toward the presentation surface L that coincides with the track surface C1.

Figure 7B:
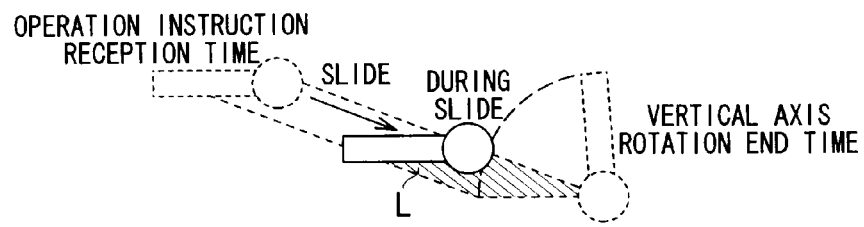

FIG. 7B shows, like FIG. 4B, the C-arm 26 at a position coordinate and a vertical axis rotation angle during a slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 7B, the presentation surface calculating unit 66 during the slide calculates the presentation surface L as a track surface portion from during the slide until the time of the end of the slide in the track surface C1. The irradiation control unit during the slide controls the laser beam source 33 to continuously and intermittently irradiate a laser beam toward the presentation surface L as a part of the track surface C1.

Figure 7C:
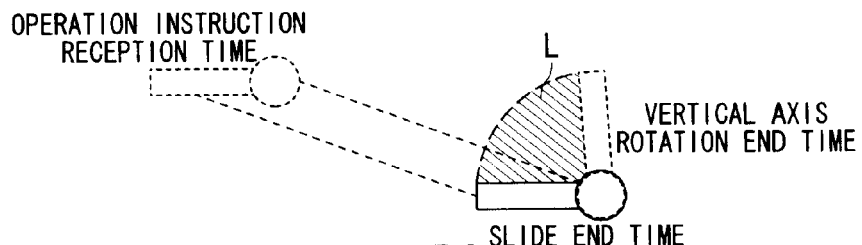

FIG. 7C shows, like FIG. 4C, the C-arm 26 at a position coordinate and a vertical axis rotation angle at the time of end of the slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 7C, the presentation surface calculating unit 66 at the time of the end of the slide calculates the presentation surface L that coincides with the track surface C2 calculated by the track surface calculating unit 65. The irradiation control unit 67 at the time of the end of the slide controls the laser beam source 33 to switch irradiation on the track surface C1 to irradiation on the track surface C2 and continuously or intermittently irradiate a laser beam toward the presentation surface L that coincides with the track surface C2.

Figure 7D:
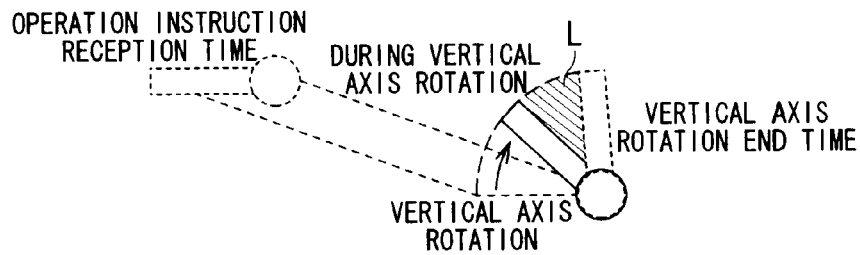

FIG. 7D shows, like FIG. 4D, the C-arm 26 at a position coordinate and a vertical axis rotation angle during vertical axis rotation (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 7D, the presentation surface calculating unit 66 during the vertical axis rotation calculates the presentation surface L as a track surface portion from during the vertical axis rotation until the time of the end of the vertical axis rotation in the track surface C2. The irradiation control unit 67 during the vertical axis rotation controls the laser beam source 33 to continuously or intermittently irradiate a laser beam toward the presentation surface L as a part of the track surface C2.

Figure 7E:
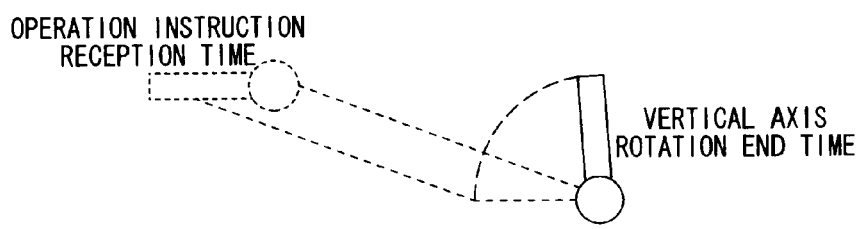

FIG. 7E shows, like FIG. 4E, the C-arm 26 at a position coordinate and a vertical axis rotation angle at the time of end of the vertical axis rotation (a solid line) and the C-arm 26 at the position coordinate and the vertical axis rotation angle at the time of the reception of the operation instruction (a broken line). As shown in FIG. 7E, the C-arm 26 at the time of the end of the vertical axis rotation is at the registered position coordinate and the registered vertical axis rotation angle and ends the movement. Therefore, the irradiation control unit 67 at the time of the end of the vertical axis rotation controls the laser beam source 33 to stop the irradiation of the laser beam.

FIGS. 8A to 8E are top views schematically showing a sample of a modification of the transition of the presentation surface shown in FIGS. 6A to 6E.

Figure 8A:
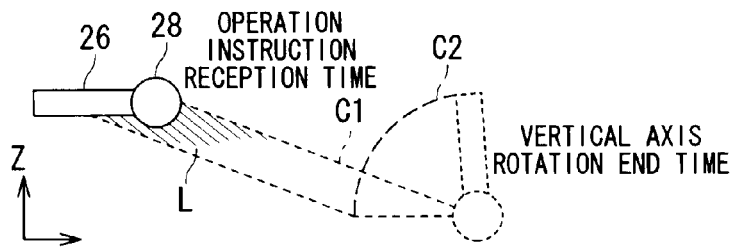
FIGS. 8A to 8E are top views schematically showing a sample of a modification of the transition of the presentation surface shown in FIGS. 6A to 6E.

FIG. 8A shows, like FIG. 4A, the C-arm 26 at a position coordinate and a vertical axis rotation angle at the time of the reception of the operation instruction (a solid line) and the C-arm 26 at the registered position coordinate and the registered vertical axis rotation angle (at the time of end of the vertical axis rotation) (a broken line). As shown in FIG. 8A, the presentation surface calculating unit 66 at the time of the reception of the operation instruction (after the calculation of the track surface C1) calculates the presentation surface L as a track surface portion from the time of the reception of the operation instruction until after elapse of a fixed period in the track surface C1 calculated by the track surface calculating unit 65. The irradiation control unit 67 at the time of the reception of the operation instruction controls the laser beam source 33 to continuously or intermittently irradiate a laser beam toward the presentation surface L as a part of the track surface C1.

Figure 8B:
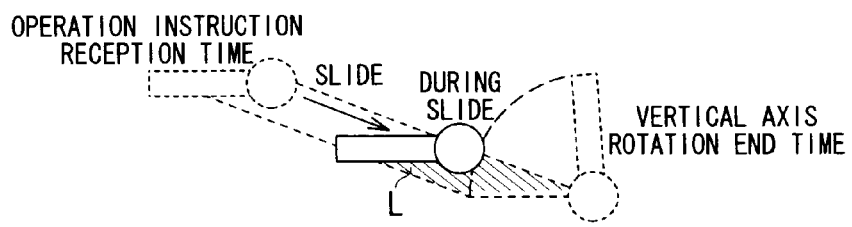

FIG. 8B shows, like FIG. 4B, the C-arm 26 at a position coordinate and a vertical axis rotation angle during a slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 8B, the presentation surface calculating unit 66 during the slide calculates the presentation surface L as a track surface portion from during the slide until after elapse of a fixed period in the track surface C1. The irradiation control unit 67 during the slide controls the laser beam source 33 to continuously and intermittently irradiate a laser beam toward the presentation surface L as a part of the track surface C1.

Figure 8C:
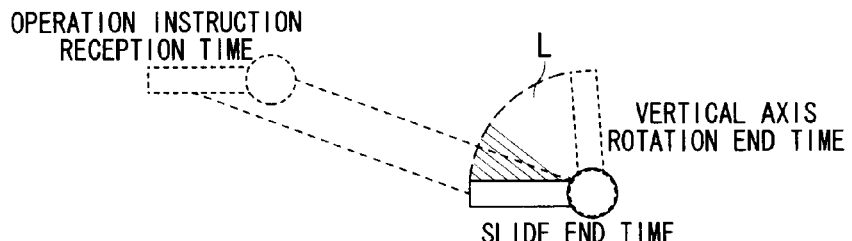

FIG. 8C shows, like FIG. 4C, the C-arm 26 at a position coordinate and a vertical axis rotation angle at the time of end of the slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 8C, the presentation surface calculating unit 66 at the time of the end of the slide calculates the presentation surface L as a track surface portion from the time of the end of the slide until after elapse of a fixed period in the track surface C2 calculated by the track surface calculating unit 65. The irradiation control unit 67 at the time of the end of the slide controls the laser beam source 33 to switch irradiation on the track surface C1 to irradiation on the track surface C2 and continuously or intermittently irradiate a laser beam toward the presentation surface L as a part of the track surface C2.

Figure 8D:
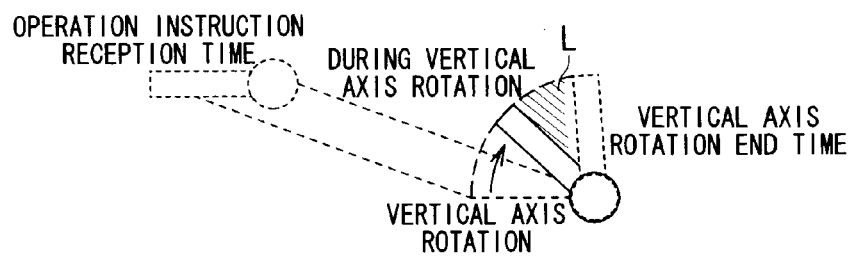

FIG. 8D shows, like FIG. 4D, the C-arm 26 at a position coordinate and a vertical axis rotation angle during vertical axis rotation (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 8D, the presentation surface calculating unit 66 during the vertical axis rotation calculates the presentation surface L as a track surface portion from during the vertical axis rotation until after elapse of a fixed period in the track surface C2. The irradiation control unit 67 during the vertical axis rotation controls the laser beam source 33 to continuously or intermittently irradiate a laser beam toward the presentation surface L as a part of the track surface C2.

Figure 8E:
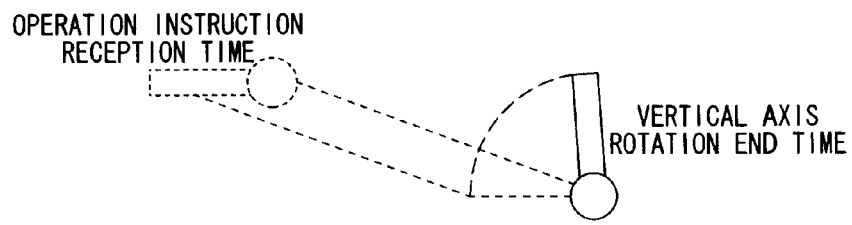

FIG. 8E shows, like FIG. 4E, the C-arm 26 at a position coordinate and a vertical axis rotation angle at the time of end of the vertical axis rotation (a solid line) and the C-arm 26 at the position coordinate and the vertical axis rotation angle at the time of the reception of the operation instruction (a broken line). As shown in FIG. 8E, the C-arm 26 at the time of the end of the vertical axis rotation is at the registered position coordinate and the registered vertical axis rotation angle and ends the movement. Therefore, the irradiation control unit 67 at the time of the end of the vertical axis rotation controls the laser beam source 33 to stop the irradiation of the laser beam.

Figure 9:
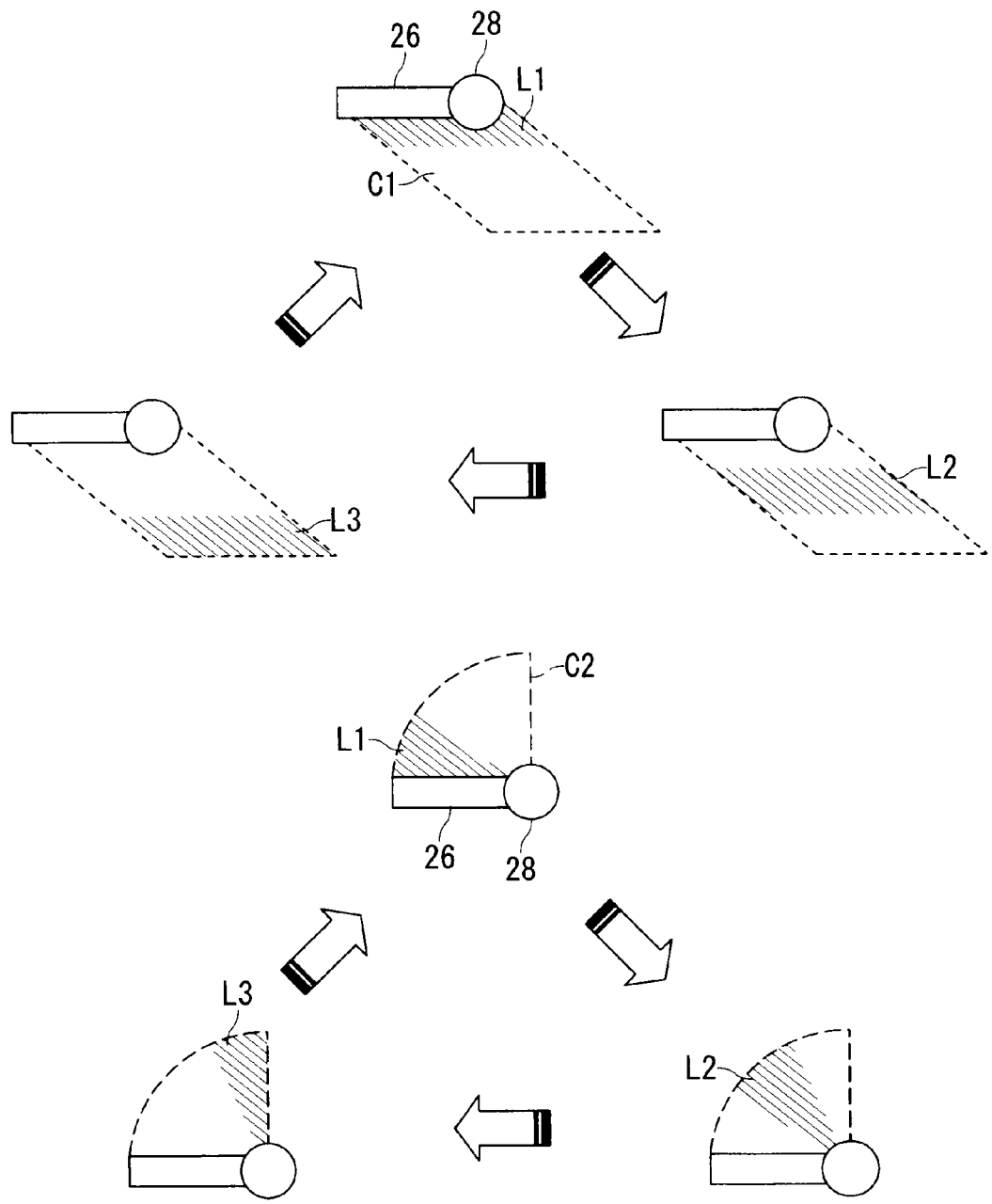
FIG. 9 is a top view schematically showing a sample of a modification of the transition of the presentation surface shown in FIGS. 6A to 6E.

FIG. 9 is a top view schematically showing a modification of the transition of the presentation surface shown in FIGS. 6A to 6E.

As shown in an upper section of FIG. 9, the presentation surface calculating unit 66 divides the track surface C1 shown in FIG. 6A (the track surface portion of the track surface C1 shown in FIGS. 7A and 8A) into rectangular presentation surfaces L1, L2, and L3 in order from one closest to the C-arm 26. Then, the irradiation control unit 67 controls the laser beam source 33 to cyclically irradiate a laser beam from the presentation surface L1 toward the presentation surface L3. As shown in a lower section of FIG. 9, the presentation surface calculating unit 66 divides the track surface C2 shown in FIG. 6A (the track surface portion of the track surface C2 shown in FIGS. 7A and 8A) into fan-shaped presentation surfaces L1, L2, and L3 in order from one closest to the C-arm 26. Then, the irradiation control unit 67 controls the laser beam source 33 to cyclically irradiate a laser beam from the presentation surface L1 toward the presentation surface L3. With the cyclic irradiation shown in FIG. 9, there is an effect that a proceeding direction of the operation of the C-arm 26 becomes clearer for the operator.

FIGS. 10A to 10E are top views schematically showing the transition of the presentation surface that occurs when the second time chart shown in FIG. 5B is used.

Figure 10A:
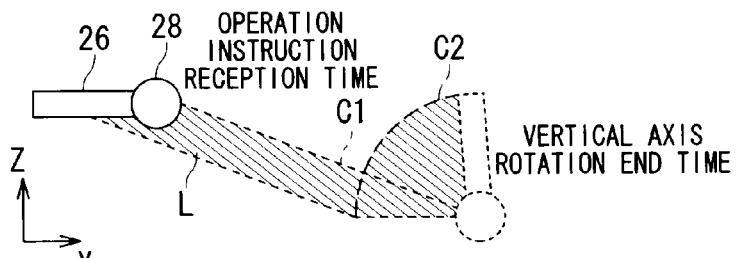
FIGS. 10A to 10E are top views schematically showing a transition of a presentation surface that occurs when the second time chart shown in FIG. 5B is used.

FIG. 10A shows, like FIG. 4A, the C-arm 26 at a position coordinate and a vertical axis rotation angle at the time of the reception of the operation instruction (a solid line) and the C-arm 26 at the registered position coordinate and the registered vertical axis rotation angle (at the time of end of the vertical axis rotation) (a broken line). As shown in FIG. 10A, the presentation surface calculating unit 66 at the time of the reception of the operation instruction (after the calculation of the track surface C) calculates the presentation surface L that coincides with the track surface C calculated by the track surface calculating unit 65. The irradiation control unit 67 at the time of the reception of the operation instruction controls the laser beam source 33 to continuously or intermittently irradiate a laser beam toward the presentation surface L that coincides with the track surface C.

Figure 10B:
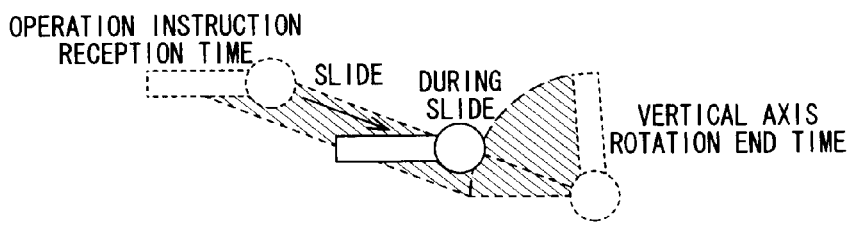

FIG. 10B shows, like FIG. 4B, the C-arm 26 at a position coordinate and a vertical axis rotation angle during a slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 10B, the irradiation control unit 67 during the slide controls the laser beam source 33 to continuously and intermittently irradiate a laser beam toward the presentation surface L that coincides with the track surface C.

Figure 10C:
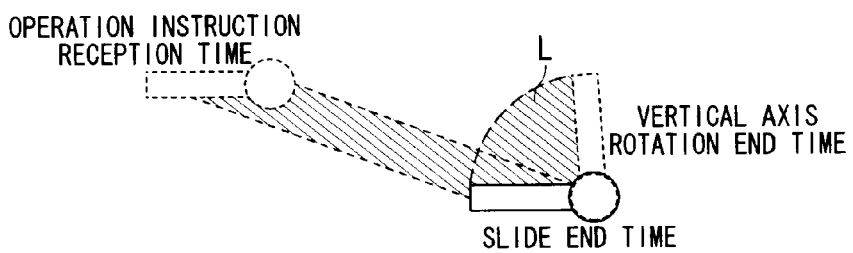

FIG. 10C shows, like FIG. 4C, the C-arm 26 at a position coordinate and a vertical axis rotation angle at the time of end of the slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 10O, the irradiation control unit 67 at the time of the end of the slide controls the laser beam source 33 to continuously or intermittently irradiate a laser beam toward the presentation surface L that coincides with the track surface C.

Figure 10D:
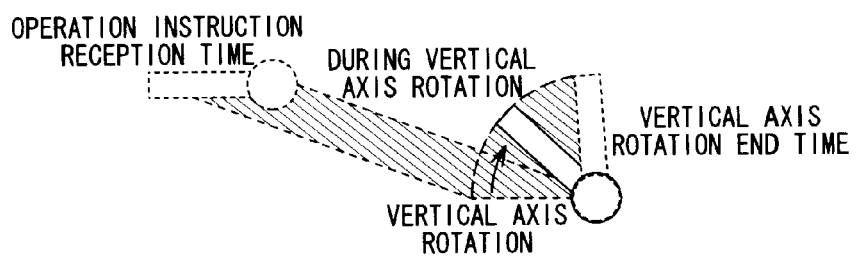

FIG. 10D shows, like FIG. 4D, the C-arm 26 at a position coordinate and a vertical axis rotation angle during vertical axis rotation (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 10D, the irradiation control unit 67 during the vertical axis rotation controls the laser beam source 33 to continuously or intermittently irradiate a laser beam toward the presentation surface L that coincides with the track surface C.

Figure 10E:
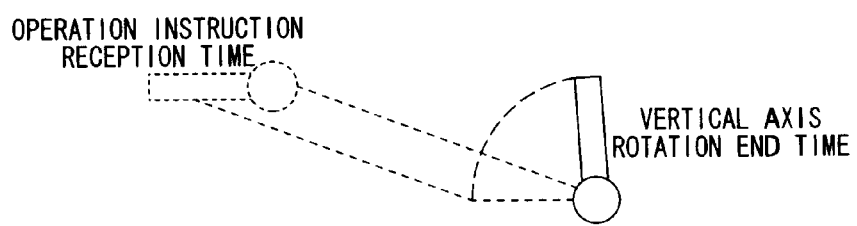

FIG. 10E shows, like FIG. 4E, the C-arm 26 at a position coordinate and a vertical axis rotation angle at the time of end of the vertical axis rotation (a solid line) and the C-arm 26 at the position coordinate and the vertical axis rotation angle at the time of the reception of the operation instruction (a broken line). As shown in FIG. 10E, the C-arm 26 at the time of the end of the vertical axis rotation is at the registered position coordinate and the registered vertical axis rotation angle and ends the movement. Therefore, the irradiation control unit 67 at the time of the end of the vertical axis rotation controls the laser beam source 33 to stop the irradiation of the laser beam.

In the explanation with reference to FIGS. 10A to 10E, the track surface C and the presentation surface L are always set to coincide with each other. However, the present invention is not limited to this. Modifications are explained with reference to FIGS. 11A to 11E and FIGS. 12A to 12E.

FIGS. 11A to 11E are top views schematically showing modifications of the transition of the presentation surface shown in FIGS. 10A to 10E.

Figure 11A:
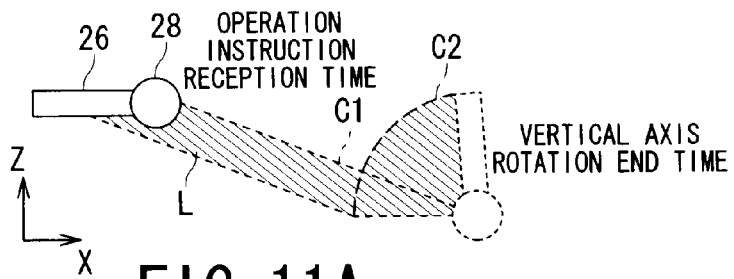
FIGS. 11A to 11E are top views schematically showing a sample of a modification of the transition of the presentation surface shown in FIGS. 10A to 10E.

FIG. 11A shows, like FIG. 4A, the C-arm 26 at a position coordinate and a vertical axis rotation angle at the time of the reception of the operation instruction (a solid line) and the C-arm 26 at the registered position coordinate and the registered vertical axis rotation angle (at the time of end of the vertical axis rotation) (a broken line). As shown in FIG. 11A, the presentation surface calculating unit 66 at the time of the reception of the operation instruction (after the calculation of the track surface C) calculates the presentation surface L that coincides with the track surface C calculated by the track surface calculating unit 65. The irradiation control unit 67 at the time of the reception of the operation instruction controls the laser beam source 33 to continuously or intermittently irradiate a laser beam toward the presentation surface L that coincides with the track surface C.

Figure 11B:
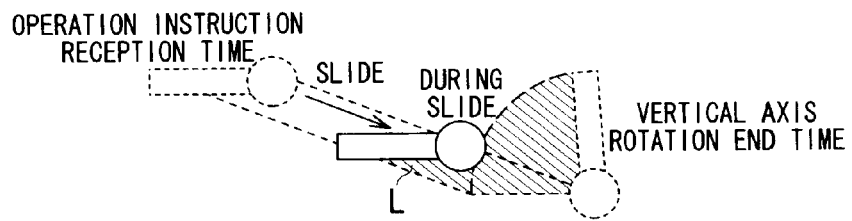

FIG. 11B shows, like FIG. 4B, the C-arm 26 at a position coordinate and a vertical axis rotation angle during a slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 11B, the presentation surface calculating unit 66 during the slide calculates the presentation surface L as a track surface portion (a part of the track surface C1 and the entire track surface C2) from during the slide until the time of the end of the vertical axis rotation. The irradiation control unit 67 during the slide controls the laser beam source 33 to continuously and intermittently irradiate a laser beam toward the presentation surface L as a part of the track surface C.

Figure 11C:
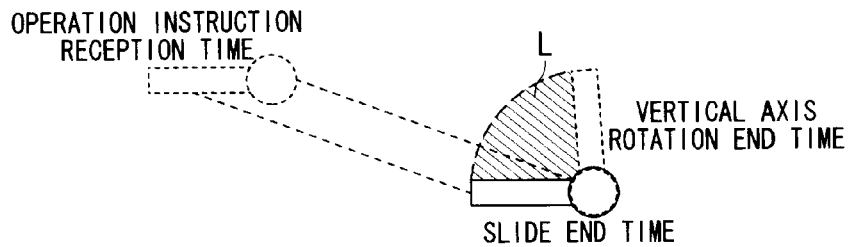

FIG. 11C shows, like FIG. 4C, the C-arm 26 at a position coordinate and a vertical axis rotation angle at the time of end of the slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 11C, the presentation surface calculating unit at the time of the end of the slide calculates the presentation surface L as a track surface portion (the entire track surface C2) from the time of the end of the slide until the time of the end of the vertical axis rotation. The irradiation control unit 67 at the time of the end of the slide controls the laser beam source 33 to continuously or intermittently irradiate a laser beam toward the presentation surface L as a part of the track surface C.

Figure 11D:
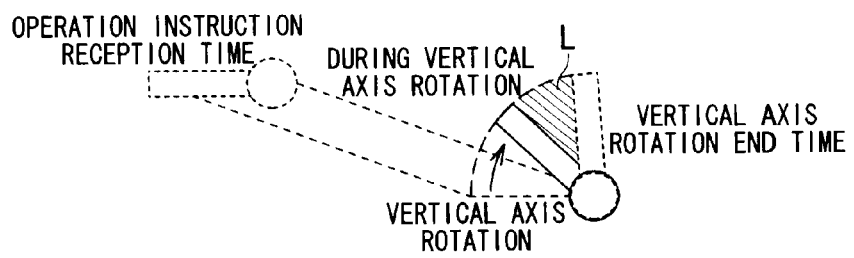

FIG. 11D shows, like FIG. 4D, the C-arm 26 at a position coordinate and a vertical axis rotation angle during vertical axis rotation (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 11D, the presentation surface calculating unit 66 during the vertical axis rotation calculates the presentation surface L as a track surface portion (a part of the track surface C2) from during the vertical axis rotation until the time of the end of the vertical axis rotation. The irradiation control unit 67 during the vertical axis rotation controls the laser beam source 33 to continuously or intermittently irradiate a laser beam toward the presentation surface L as a part of the track surface C.

Figure 11E:
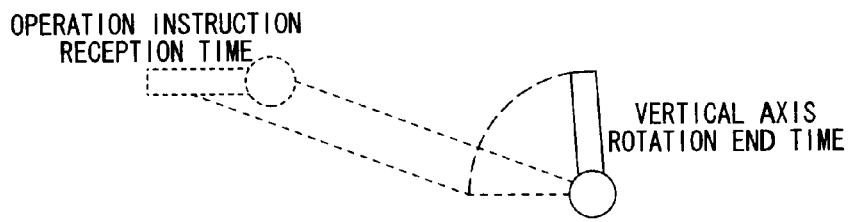

FIG. 11E shows, like FIG. 4E, the C-arm 26 at a position coordinate and a vertical axis rotation angle at the time of end of the vertical axis rotation (a solid line) and the C-arm 26 at the position coordinate and the vertical axis rotation angle at the time of the reception of the operation instruction (a broken line). As shown in FIG. 11E, the C-arm 26 at the time of the end of the vertical axis rotation is at the registered position coordinate and the registered vertical axis rotation angle and ends the movement. Therefore, the irradiation control unit 67 at the time of the end of the vertical axis rotation controls the laser beam source 33 to stop the irradiation of the laser beam.

FIGS. 12A to 12E are top views schematically showing modifications of the transition of the presentation surface shown in FIGS. 10A to 10E.

Figure 12A:
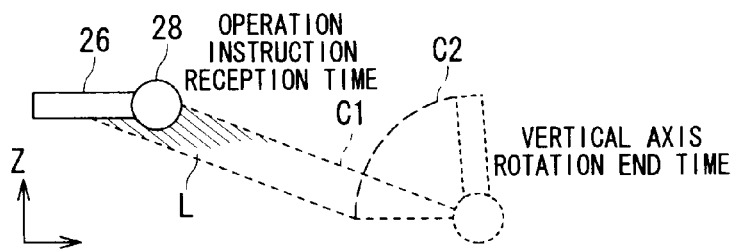
FIGS. 12A to 12E are top views schematically showing a sample of a modification of the transition of the presentation surface shown in FIGS. 10A to 10E.

FIG. 12A shows, like FIG. 4A, the C-arm 26 at a position coordinate and a vertical axis rotation angle at the time of the reception of the operation instruction (a solid line) and the C-arm 26 at the registered position coordinate and the registered vertical axis rotation angle (at the time of end of the vertical axis rotation) (a broken line). As shown in FIG. 12A, the presentation surface calculating unit 66 at the time of the reception of the operation instruction (after the calculation of the track surface C) calculates the presentation surface L as a track surface portion (a part of the track surface C1) from the time of the reception of the operation instruction until elapse of a fixed period in the track surface C calculated by the track surface calculating unit 65. The irradiation control unit 67 at the time of the reception of the operation instruction controls the laser beam source 33 to continuously or intermittently irradiate a laser beam toward the presentation surface L as a part of the track surface C.

Figure 12B:
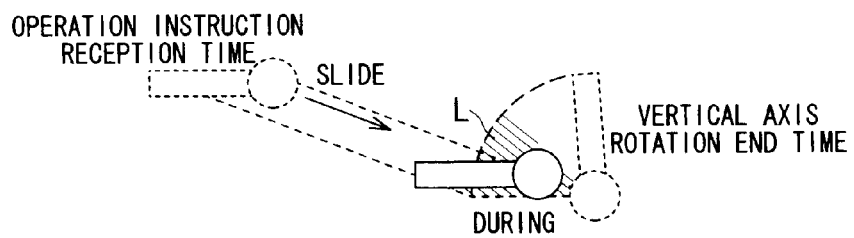

FIG. 12B shows, like FIG. 4B, the C-arm 26 at a position coordinate and a vertical axis rotation angle during a slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 12B, the presentation surface calculating unit 66 during the slide calculates the presentation surface L as a track surface portion (a part of the track surface C1 and a part of the track surface C2) from during the slide until after elapse of a fixed period. The irradiation control unit 67 during the slide controls the laser beam source 33 to continuously and intermittently irradiate a laser beam toward the presentation surface L as a part of the track surface C.

Figure 12C:
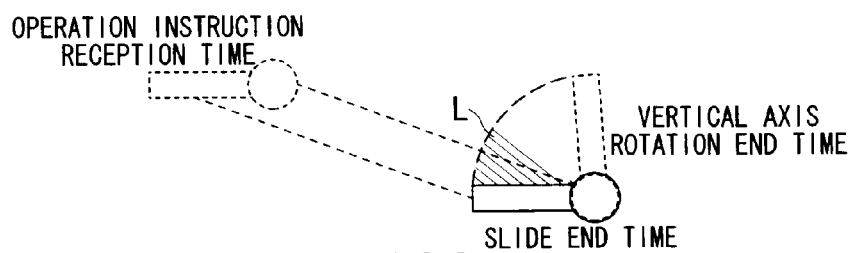

FIG. 12C shows, like FIG. 4C, the C-arm 26 at a position coordinate and a vertical axis rotation angle at the time of end of the slide (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 12C, the presentation surface calculating unit 66 at the time of the end of the slide calculates the presentation surface L as a track surface portion (a part of the track surface C2) from the time of the end of the slide until after elapse of a fixed period. The irradiation control unit 67 at the time of the end of the slide controls the laser beam source 33 to continuously or intermittently irradiate a laser beam toward the presentation surface L as a part of the track surface C.

Figure 12D:
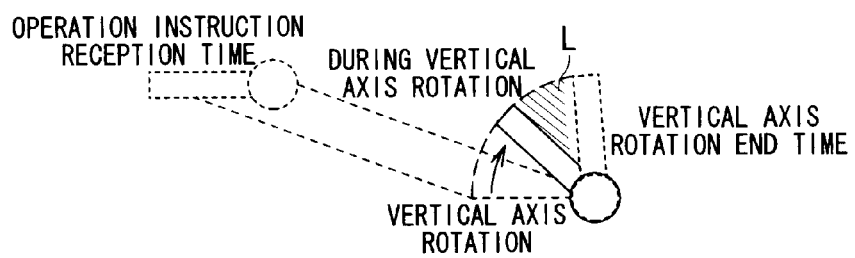

FIG. 12D shows, like FIG. 4D, the C-arm 26 at a position coordinate and a vertical axis rotation angle during vertical axis rotation (a solid line), the C-arm 26 at the position coordinate and the vertical axis rotation angle at the time of the reception of the operation instruction (a broken line), and the C-arm 26 at the registered position coordinate and the registered vertical axis rotation angle (a broken line). As shown in FIG. 12D, the presentation surface calculating unit 66 during the vertical axis rotation calculates the presentation surface L as a track surface portion (a part of the track surface C2) from during the vertical axis rotation until after elapse of a fixed period. The irradiation control unit 67 during the vertical axis rotation controls the laser beam source 33 to continuously or intermittently irradiate a laser beam toward the presentation surface L as a part of the track surface C.

Figure 12E:
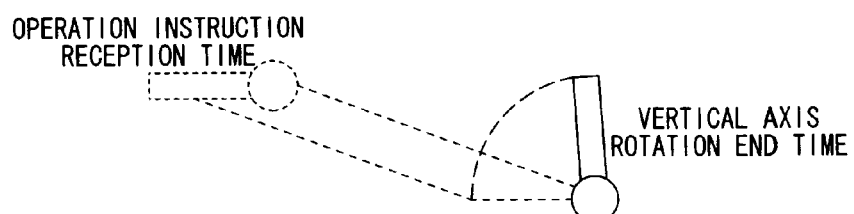

FIG. 12E shows, like FIG. 4E, the C-arm 26 at position coordinate and a vertical axis rotation angle at the time of end of the vertical axis rotation (a solid line) and the C-arm 26 at the position coordinate and the vertical axis rotation angle at the time of the reception of the operation instruction (a broken line). As shown in FIG. 12E, the C-arm 26 at the time of the end of the vertical axis rotation is at the registered position coordinate and the registered vertical axis rotation angle and ends the movement. Therefore, the irradiation control unit 67 at the time of the end of the vertical axis rotation controls the laser beam source 33 to stop the irradiation of the laser beam.

Figure 13:
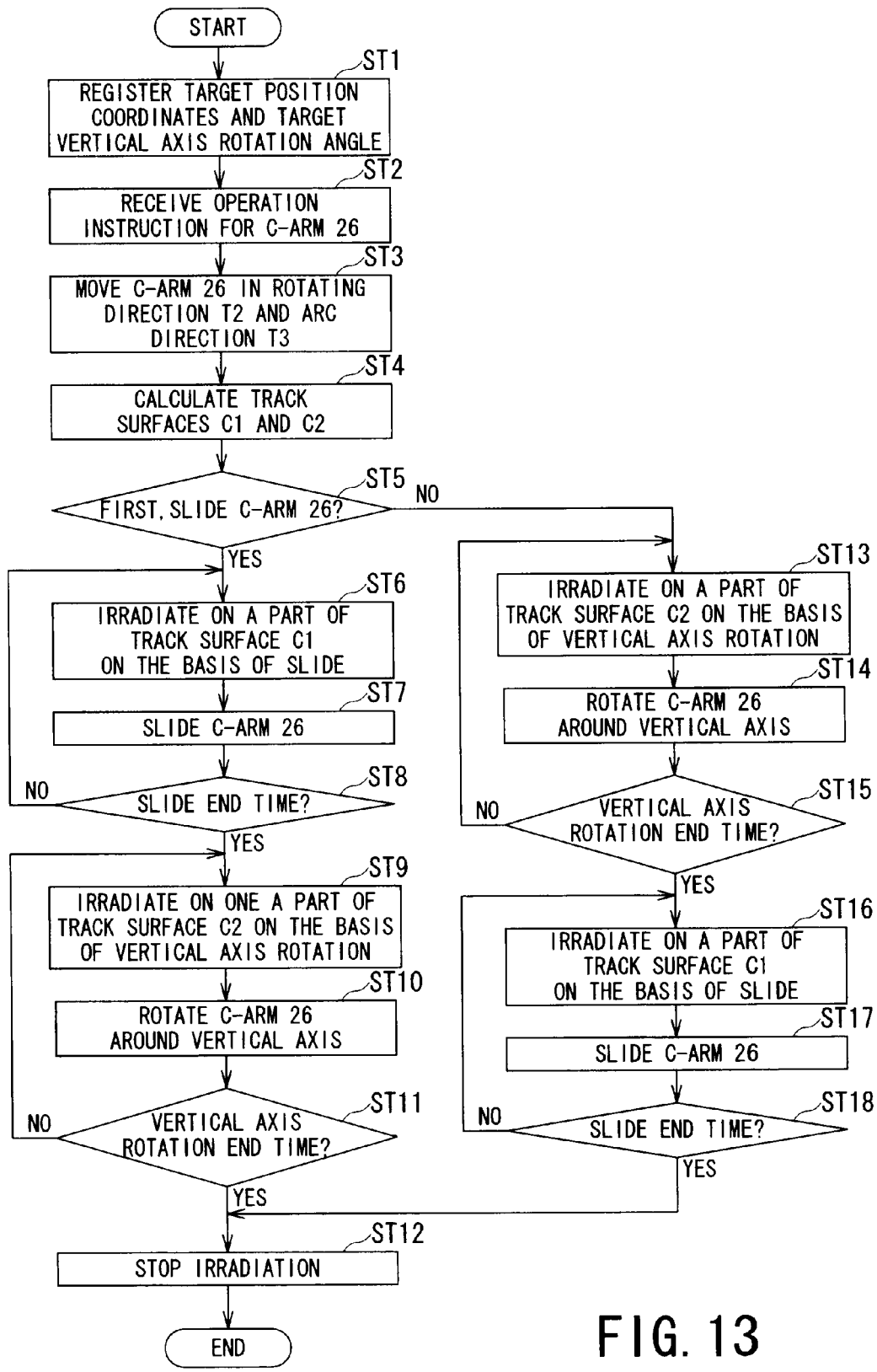
FIG. 13 is a flowchart showing operations of the X-ray image diagnostic apparatus according to the present embodiment.

The operation shown in FIGS. 7A to 7E in the X-ray image diagnostic apparatus 10 according to the present embodiment is explained with reference to a flowchart shown in FIG. 13.

First, the X-ray image diagnostic apparatus 10 registers in advance, according to operation of the operator via the input device 44, a target position after movement of the C-arm 26, for example, a target position coordinate and a target vertical axis rotation angle (or target position coordinates and target vertical axis rotation angles) (step ST1).

Subsequently, the X-ray image diagnostic apparatus 10 receives, according to operation of the operator via the input device 44, an operation instruction for movement from a present position coordinate and a present vertical axis rotation angle of the C-arm 26 to the position coordinate and the vertical axis rotation angle registered in step ST1 (step ST2).

When the X-ray image diagnostic apparatus 10 receives the movement instruction for the C-arm 26 in step ST2, the X-ray image diagnostic apparatus 10 moves the C-arm 26 in the rotating direction T2 and the arc direction T3 to align the carriage 213, the X-ray irradiating device 27, and the receiving device 28 on a straight line when the operation instruction is received by the operation instruction receiving unit 62 (step ST3).

The X-ray image diagnostic apparatus 10 calculates the track surface C1 obtained by projecting a track of the C-arm 26 slid to the registered position coordinates to the floor surface and calculates the track surface C2 obtained by projecting a track of the C-arm 26 rotated around the vertical axis to the registered vertical axis rotation angle to the floor surface (step ST4).

The X-ray image diagnostic apparatus 10 determines, prior to the vertical axis rotation of the C-arm 26 to the registered vertical axis rotation angle, whether the C-arm 26 is slid to the registered position coordinate (step ST5).

When the X-ray image diagnostic apparatus 10 determines in step ST5 that the C-arm 26 is slid prior to the vertical axis rotation of the C-arm 26 (Yes in step ST5), the X-ray image diagnostic apparatus 10 controls the laser beam source 33 to spatially irradiate a laser beam toward a track surface portion from a real time between the time of the reception of the operation instruction and the time of end of the slide until after elapse of a fixed period and forms the presentation surface L in a part of the track surface C1 (step ST6).

The X-ray image diagnostic apparatus 10 drives the slide mechanism 21 and slides the carriage 213 to slide the C-arm 26 (step ST7). The X-ray image diagnostic apparatus 10 determines whether the slid C-arm 26 coincides with the registered position coordinate and the slide ends (step ST8). When the X-ray image diagnostic apparatus 10 determines in step ST8 that the slide ends (Yes in step ST8), the X-ray image diagnostic apparatus 10 controls the laser beam source 33 to spatially irradiate a laser beam toward a track surface portion from a real time between the time of the end of the slide and the time of the end of the vertical axis rotation until after elapse of a fixed period and forms the presentation surface L in a part of the track surface C2 (step ST9).

The X-ray image diagnostic apparatus 10 drives the vertical axis rotating mechanism 23 to rotate the C-arm 26 around the vertical axis (step ST10). The X-ray image diagnostic apparatus 10 determines whether the C-arm 26 rotated around the vertical axis coincides with the registered vertical axis rotation angle and the vertical axis rotation ends (step ST11). When the X-ray image diagnostic apparatus 10 determines in step ST11 that the vertical axis rotation ends (YES in step ST11), the X-ray image diagnostic apparatus 10 determines that the C-arm 26 is at the registered position coordinate and the registered vertical axis rotation angle and ends the movement. The X-ray image diagnostic apparatus 10 stops the irradiation of the laser beam at the time of the end of the vertical axis rotation (step ST12) and ends the operation.

On the other hand, when the X-ray image diagnostic apparatus 10 determines in step ST5 that the C-arm 26 is not slid prior to the vertical axis rotation of the C-arm 26 (No in step ST5), the X-ray image diagnostic apparatus 10 controls the laser beam source 33 to spatially irradiate a laser beam toward a track surface portion from a real time between the time of the reception of the operation instruction and the time of the end of the vertical axis rotation until after elapse of a fixed period and forms the presentation surface L in a part of the track surface C2 (step ST13).

The X-ray image diagnostic apparatus 10 drives the vertical axis rotating mechanism 23 and rotates the C-arm 26 around the vertical axis (step ST14). The X-ray image diagnostic apparatus 10 determines whether the C-arm 26 rotated around the vertical axis coincides with the registered vertical axis rotation angle and the vertical axis rotation ends (step ST15). When the X-ray image diagnostic apparatus 10 determines that the vertical axis rotation ends (Yes in step ST15), the X-ray image diagnostic apparatus 10 controls the laser beam source 33 to spatially irradiate a laser beam toward a track surface portion from a real time between the time of the end of the vertical axis rotation and the time of the end of the slide until after elapse of a fixed period and forms the presentation surface L in a part of the track surface C1 (step ST16).

The X-ray image diagnostic apparatus 10 drives the slide mechanism 21 and slides the carriage 213 to slide the C-arm 26 (step ST17). The X-ray image diagnostic apparatus 10 determines whether the slid C-arm 26 coincides with the registered position coordinate and the slide ends (step ST18). When the X-ray image diagnostic apparatus 10 determines in step ST18 that the slide ends (Yes in step ST18), the X-ray image diagnostic apparatus 10 determines that the C-arm 26 is at the registered position coordinate and the registered vertical axis rotation angle and ends the movement. The X-ray image diagnostic apparatus 10 stops the irradiation of the laser beam (step ST12) and ends the operation.

When the X-ray image diagnostic apparatus 10 determines in steps ST8 and ST18 that the slide does not end (No in steps ST8 and ST18), the X-ray image diagnostic apparatus 10 controls the laser beam source 33 to irradiate a laser beam toward a track surface portion from a next real time until after elapse of a fixed period in the track surface C1 calculated in step ST4 and forms the presentation surface L in a part of the track surface C1 (steps ST6 and ST16).

When the X-ray image diagnostic apparatus 10 determines in steps ST11 and ST15 that the vertical axis rotation does not end (No in steps ST11 and ST15), the X-ray image diagnostic apparatus 10 controls the laser beam source 33 to irradiate a laser beam toward a track surface portion from a next real time until after elapse of a fixed period in the track surface C2 calculated in step ST4 and forms the presentation surface L in a part of the track surface C2 (steps ST9 and ST13).

When, in step ST2, the X-ray image diagnostic apparatus 10 receives an operation instruction for movement of the C-arm 26 to a position coordinate and a vertical axis rotation angle not obstructing an operation when the surgeon performs the operation on the object P on the table-top 29a, after the end of the operation in step ST12, the X-ray image diagnostic apparatus 10 stays on standby for reception of an operation instruction for the C-arm 26 in next step ST2. On the other hand, when, in step ST2, the X-ray image diagnostic apparatus 10 receives an operation instruction for movement of the C-arm 26 to a position coordinate and a vertical axis rotation angle for enabling the surgeon to immediately start photographing of the object P on the table-top 29a, the X-ray image diagnostic apparatus 10 starts collection of a fluoroscopic image and a photographing image after the end of the operation in step ST12.

The presentation surface calculating unit 66 shown in FIG. 3 also displays the presentation surface L calculated on the basis of the track surfaces C, C1, and C2 on the display device 54 together with the C-arm 26.

FIGS. 14A to 14E are diagrams schematically showing a sample of a display screen including the presentation surface L.

Figure 14A:
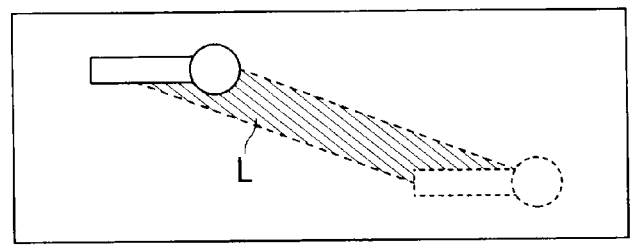
FIGS. 14A to 14E are diagrams schematically showing a sample of a display screen including the presentation surface.

FIG. 14A shows a display surface of the C-arm 26 at the position coordinate and the vertical axis rotation angle at the time of the reception of the operation instruction (a solid line), the C-arm 26 at the registered position coordinate and the registered vertical axis rotation angle (at the time of the end of the vertical axis rotation) (a broken line), and the presentation surface L that coincides with the track surface C1 calculated by the track surface calculating unit 65. As shown in FIG. 14A, at the time of the reception of the operation instruction (after the calculation of the track surface C1), the presentation surface calculating unit 66 calculates the presentation surface L that coincides with the track surface C1 calculated by the track surface calculating unit 65. At the time of the reception of the operation instruction, the display device 54 schematically displays the C-arm 26 at the time of the reception of the operation instruction and the presentation surface L that coincides with the track surface C1.

Figure 14B:
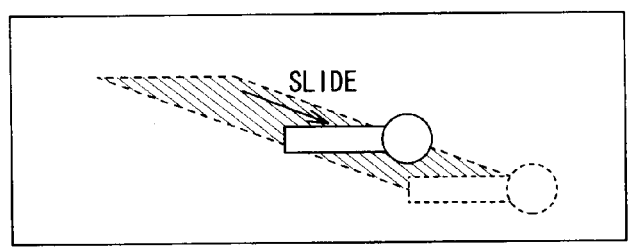

FIG. 14B shows a display screen of the C-arm 26 at the position coordinate and the vertical axis rotation angle during the slide (a solid line), the C-arm 26 at the registered position coordinate and the registered vertical axis rotation angle (a broken line), and the presentation surface L that coincides with the track surface C1. As shown in FIG. 14B, during the slide, the display device 54 schematically displays the C-arm 26 during the slide and the presentation surface L that coincides with the track surface C1 calculated by the track surface calculating unit 65.

Figure 14C:
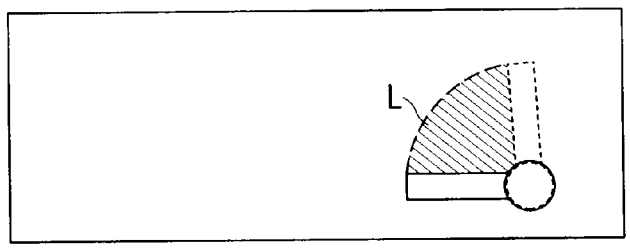

FIG. 14C shows a display screen of the C-arm 26 at the position coordinate and the vertical axis rotation angle at the time of the end of the slide (a solid line), the C-arm 26 at the registered position coordinate and the registered vertical axis rotation angle (a broken line), and the presentation surface L that coincides with the track surface C2 calculated by the track surface calculating unit 65. As shown in FIG. 14C, during the slide, the display device 54 switches display of the track surface C1 to display of the track surface C2 and schematically displays the presentation surface L that coincides with the track surface C2 and the C-arm 26 at the end of the slide.

Figure 14D:
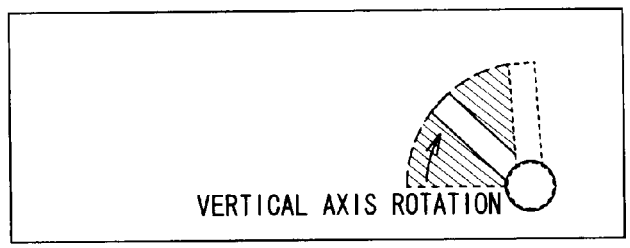

FIG. 14D shows a display screen of the C-arm 26 at the position coordinate and the vertical axis rotation angle during the vertical axis rotation (a solid line), the C-arm 26 at the registered position coordinate and the registered vertical axis rotation angle (a broken line), and the presentation surface L that coincides with the track surface C2 calculated by the track surface calculating unit 65. As shown in FIG. 14D, during the vertical axis rotation, the display device 54 schematically displays the C-arm 26 during the vertical axis rotation and the presentation surface L that coincides with the track surface C2 calculated by the track surface calculating unit 65.

Figure 14E:
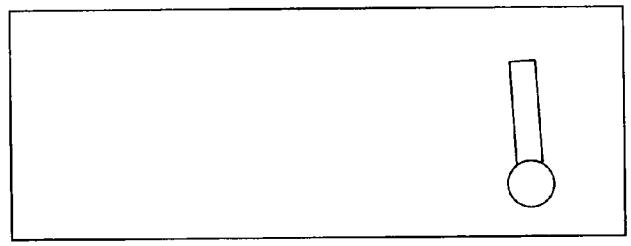

FIG. 14E shows a display screen of the C-arm 26 at the registered position coordinate and the registered vertical axis rotation angle (a solid line). As shown in FIG. 14E, at the time of the end of the vertical axis rotation, the display device 54 schematically displays only the C-arm 26 at the time of the end of the slide.

In the explanation with reference to FIGS. 14A to 14E, the track surfaces C1 and C2 and the presentation surface L are always set to coincide with each other. However, the present invention is not limited to this.

With the X-ray image diagnostic apparatus 10 according to the present embodiment, a track of future movement of the C-arm 26 is presented to the operator as the presentation surface L1. Therefore, necessity of movement of an obstacle on the track is clarified for the operator. In particular, the laser beam source 33 irradiates a laser beam toward the presentation surface L. Therefore, when an obstacle is present on a moving path of the C-arm 26, since the laser beam is directly irradiated on the obstacle, necessity of movement of the obstacle on the track is clarified. Consequently, with the X-ray image diagnostic apparatus 10, since it is possible to use the auto-positioning function while preventing collision with equipment and medical staff present in a surgical operating room, it is possible to effectively and efficiently carry out an examination and treatment for the object P.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray image diagnostic apparatus comprising:
    an X-ray irradiating unit configured to irradiate an X-ray;
    a receiving unit configured to receive the X-ray;
    a supporting unit configured to support the X-ray irradiating unit and the receiving unit to be opposed to each other, the supporting unit being movable in a room;
    a registering unit configured to register in advance a target position after movement of the supporting unit;
    a calculating unit configured to calculate a track of the supporting unit from a present position to the registered target position; and
    a presenting unit configured to present the track until the supporting unit moves to reach the registered target position.

2. The X-ray image diagnostic apparatus according to claim 1, wherein
    the registering unit registers a target position coordinate and a target vertical axis rotation angle of the supporting unit as the target position;
    the calculating unit calculates a slide track of the supporting unit from a present position coordinate to the registered target position coordinate of the supporting unit and a vertical axis rotation track of the supporting unit from a present vertical axis rotation angle of the supporting unit to the registered target vertical axis rotation angle, and
    the presenting unit presents at least one of the slide track and the vertical axis rotation track while the supporting unit is slid to the registered target position coordinate and is rotated around a vertical axis to the registered target vertical axis rotation angle.

3. The X-ray image diagnostic apparatus according to claim 2, wherein
    the presenting unit is included in the supporting unit and irradiates a laser beam toward a floor surface or a ceiling surface on which the slide track or the vertical axis rotation track is projected.

4. The X-ray image diagnostic apparatus according to claim 2, wherein
    the presenting unit displays the supporting unit, the slide track, and the vertical axis rotation track on a monitor set in the room.

5. The X-ray image diagnostic apparatus according to claim 2, wherein
    the presenting unit presents only the slide track during the slide and presents only the vertical axis rotation track during the vertical axis rotation.

6. The X-ray image diagnostic apparatus according to claim 2, wherein
    the presenting unit presents, during the slide, only the slide track from a real-time present coordinate to the registered target position coordinate of the supporting unit and presents, during the vertical axis rotation, only the vertical axis rotation track from a real-time vertical axis rotation angle to the registered target vertical axis rotation angle of the supporting unit.

7. The X-ray image diagnostic apparatus according to claim 2, wherein
    the presenting unit presents, during the slide, the slide track included from a real-time position coordinate of the supporting unit until after elapse of a fixed time and presents, during the vertical axis rotation, the vertical axis rotation track included from a real-time vertical axis rotation angle of the supporting unit until after elapse of a fixed time.

8. The X-ray image diagnostic apparatus according to claim 1, further comprising:
    an input unit configured to switch presentation and non-presentation of the track, wherein
    the presenting unit switches the presentation and the non-presentation of the track according to an instruction from the input unit.

9. The X-ray image diagnostic apparatus according to claim 1, wherein
    the presenting unit switches, according to whether the track calculated by the calculating unit is equal to or longer than a predetermined distance, presentation and non-presentation of the track.

10. A control method of an X-ray image diagnostic apparatus having: an X-ray irradiating unit configured to irradiate an X-ray; a receiving unit configured to receive the X-ray; and a supporting unit configured to support the X-ray irradiating unit and the receiving unit to be opposed to each other, the supporting unit being movable in a room, comprising:
    a registering step for registering in advance a target position after movement of the supporting unit;
    a calculating step for calculating a track of the supporting unit from a present position to the registered target position; and
    a presenting step for presenting the track until the supporting unit moves to reach the registered target position.

11. The control method according to claim 10, wherein
    the registering step registers a target position coordinate and a target vertical axis rotation angle of the supporting unit as the target position;
    the calculating step calculates a slide track of the supporting unit from a present position coordinate to the registered target position coordinate of the supporting unit and a vertical axis rotation track of the supporting unit from a present vertical axis rotation angle of the supporting unit to the registered target vertical axis rotation angle, and
    the presenting step presents at least one of the slide track and the vertical axis rotation track while the supporting unit is slid to the registered target position coordinate and is rotated around a vertical axis to the registered target vertical axis rotation angle.

12. The control method according to claim 11, wherein
    the presenting step irradiates a laser beam toward a floor surface or a ceiling surface on which the slide track or the vertical axis rotation track is projected.

13. The control method according to claim 11, wherein
    the presenting step displays the supporting unit, the slide track, and the vertical axis rotation track on a monitor set in the room.

14. The control method according to claim 11, wherein
    the presenting step presents only the slide track during the slide and presents only the vertical axis rotation track during the vertical axis rotation.

15. The control method according to claim 11, wherein
    the presenting step presents, during the slide, only the slide track from a real-time present coordinate to the registered target position coordinate of the supporting unit and presents, during the vertical axis rotation, only the vertical axis rotation track from a real-time vertical axis rotation angle to the registered target vertical axis rotation angle of the supporting unit.

16. The control method according to claim 11, wherein the presenting step presents, during the slide, the slide track included from a real-time position coordinate of the supporting unit until after elapse of a fixed time and presents, during the vertical axis rotation, the vertical axis rotation track included from a real-time vertical axis rotation angle of the supporting unit until after elapse of a fixed time.

17. The control method according to claim 10, wherein the presenting step switches presentation and non-presentation of the track.

18. The control method according to claim 10, wherein the presenting step switches, according to whether the track calculated by the calculating step is equal to or longer than a predetermined distance, presentation and non-presentation of the track.

* * * * *